US012612627B2

(12) United States Patent
Dudley et al.

(10) Patent No.: US 12,612,627 B2
(45) Date of Patent: Apr. 28, 2026

(54) COMPOSITIONS AND METHODS FOR INCREASING SODIUM CURRENT IN CARDIAC CELLS

(71) Applicant: REGENTS OF THE UNIVERSITY OF MINNESOTA, Minneapolis, MN (US)

(72) Inventors: Samuel C. Dudley, Minneapolis, MN (US); Gyeoung-Jin Kang, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 771 days.

(21) Appl. No.: 17/919,307

(22) PCT Filed: Apr. 19, 2021

(86) PCT No.: PCT/US2021/027905
§ 371 (c)(1),
(2) Date: Oct. 17, 2022

(87) PCT Pub. No.: WO2021/216415
PCT Pub. Date: Oct. 28, 2021

(65) Prior Publication Data
US 2023/0151364 A1 May 18, 2023

Related U.S. Application Data

(60) Provisional application No. 63/012,351, filed on Apr. 20, 2020.

(51) Int. Cl.
*C12N 15/113* (2010.01)
*A61P 9/06* (2006.01)

(52) U.S. Cl.
CPC .............. *C12N 15/113* (2013.01); *A61P 9/06* (2018.01); *C12N 2310/113* (2013.01)

(58) Field of Classification Search
None
See application file for complete search history.

(56) References Cited

U.S. PATENT DOCUMENTS

2007/0212723 A1* 9/2007 Dudley ................ C12Q 1/6883
435/325
2017/0166926 A1* 6/2017 Deverman ........... C07K 14/005

FOREIGN PATENT DOCUMENTS

WO WO-2022028472 A1 * 2/2022 ............. C12N 15/86

OTHER PUBLICATIONS

Kyrychenko et al. Cardiovascular Research 108, 324-334 (Year: 2015).*

Kang et al. JCI Insight Oct. 2020, 5(23):e140759, pp. 1-12. (Year: 2020).*
Kang et al. Circulation Research Abstract 893 vol. 125, No. supp_1, published Oct. 16, 2019 (Year: 2019).*
Zhang et al. Environ Sci Pollut Res 24:22294-22300 (Year: 2017).*
Bärta, "MiRNAsong: A web-based tool for generation and testing of miRNA sponge constructs in silico" 2016, Sci Rep, No. 6, pp. 36625.
Chachami, "Cobalt Induces Hypoxia-Inducible Factor-1 Expression in Airway Smooth Muscle Cells by a Reactive Oxygen Species- and PI3K-Dependent Mechanism", 2004, Am J Respir Cell Mol Biol, vol. 31, pp. 544-551.
Chang, "Three TF Co-expression Modules Regulate Pressure-Overload Cardiac Hypertropy in Male Mice", 2017, Sci Rep., vol. 7, 13 pages.
Chiasson, "Deficiency of MicroRNA miR-1954 Promotes Cardiac Remodeling and Fibrosis", Nov. 5, 2019, Journal of the American Heart Association, vol. 8, No. 21, 13 pages.
Daimi, "Regulation of SCN5A by microRNAs: MiR-219 modulates SCN5A transcript expression and the effects of flecainide intoxication in mice", Feb. 2015, Hearth Rhythm, vol. 2, No. 6, pp. 1333-1342.
PCT Patent Application No. PCT/US2021/027905, filed Apr. 19, 2021; International Search Report and Written Opinion issued Aug. 23, 2021; 9 pages.
PCT Patent Application No. PCT/US2021/027905, filed Apr. 19, 2021; International Preliminary Report on Patentability issued Nov. 3, 2022; 7 pages.
Kannankeril, "Mice with the R176Q cardiac ryanodine receptor mutation exhibit catecholamine-induced ventricular tachycardia and cardiomyopathy", 2006, Proc Natl Acad Sci USA, vol. 103, pp. 12179-12184.
Lee "LASAGNA-Search: an Integrated Web Tool for Transcription Factor Binding Site Search and Visualization", 2013, Biotechniques, vol. 54, pp. 141-153.
Lieve, "Gain-of-function mutation in SCN5A causes ventricular arrhythmias and early onset atrial fibrillation", 2017, International Journal of Cardiology, vol. 2, No. 36, pp. 187-193.

(Continued)

*Primary Examiner* — Brian Whiteman
(74) *Attorney, Agent, or Firm* — Mueting Raasch Group

(57) ABSTRACT

A method of increasing sodium current in a cardiac cell generally includes introducing into the cardiac cell an miR-448 inhibitor in an amount effective to decrease miR-448 suppression of SCN5A mRNA transcription, thereby increasing sodium current in the cardiac cell. A method of increasing translation of SCN5A mRNA in a cell generally includes introducing into the cell an miR-448 inhibitor in an amount effective to decrease miR-448 suppression of SCN5A mRNA transcription. A method of decreasing arrythmia in a cardiac cell generally includes introducing into the cardiac cell an miR-448 inhibitor in an amount effective to decrease miR-448 suppression of SCN5A mRNA transcription. A method of treating arrythmia in a patient having, or at risk of having, arrythmia generally includes administering to the patient an miR-448 inhibitor in an amount effective to decrease the likelihood or extent of arrythmia in the patient. In some embodiments of all methods, the miR-448 inhibitor can be an miR-448 antagomir or an miR-448 sponge.

1 Claim, 20 Drawing Sheets

Specification includes a Sequence Listing.

(56) References Cited

OTHER PUBLICATIONS

Morishima, "Atrial Fibrillation-Mediated Upregulation of MiR-30d Regulates Myocardial Electrical Remodeling of the G-Protein-Gated K+ Channel, IK.Ach", May 25, 2016, Cir J, vol. 80, No. 6, pp. 1346-1355.

Salman Ali, "Pathological microRNAs in acute cardiovascular diseases and microRNA therapeutics", 2016, Journal of Acute Disease, vol. 5, No. 1, pp. 9-15.

Woo et al., Desferrioxamine, an iron chelator, enhances HIF-1alpha accumulation via cyclooxygenase-2 signaling pathway. Biochem Biophys Res Commun 343, 8-14 (2006).

Xie, "Excessive Daytime Sleepiness Independently Predicts Increased Cardiovascular Risk After Myocardial Infarction", 2018, J Am Heart Assoc vol. 7, pp. 1-8.

Zhou, "HuR-mediated SCN5A messenger RNA stability reduces arrhythmic risk in heart failure", 2018, Heart Rhythm, vol. 15, pp. 1072-1080.

* cited by examiner (A)

(B)

(A)

A

B

C

D

FIG. 18 miRNA suppression miRNA inhibitor miRNA inhibitor (~23nt)

Ago

3' Targeted mRNA

Increased mRNA expression

SEQUENCE LISTING

```
<160> NUMBER OF SEQ ID NOS: 7

<210> SEQ ID NO 1
<211> LENGTH: 22
<212> TYPE: RNA
<213> ORGANISM: Homo sapiens

<400> SEQUENCE: 1
uugcauaugu aggauguccc au                                              22

<210> SEQ ID NO 2
<211> LENGTH: 24
<212> TYPE: RNA
<213> ORGANISM: Homo sapiens

<400> SEQUENCE: 2
gacaauccua uuuagcauau gcaa                                            24
```

-continued

```
<210> SEQ ID NO 3
<211> LENGTH: 24
<212> TYPE: RNA
<213> ORGANISM: Artificial
<220> FEATURE:
<223> OTHER INFORMATION: Polynucleotide

<400> SEQUENCE: 3
gacaauccua uuuagcuaua cgua                                           24

<210> SEQ ID NO 4
<211> LENGTH: 22
<212> TYPE: DNA
<213> ORGANISM: Artificial
<220> FEATURE:
<223> OTHER INFORMATION: Primer

<400> SEQUENCE: 4
tggttgtcat cctctccatc gt                                            22

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
atgagggcaa agagcagcgt                                               20

<210> SEQ ID NO 6
<211> LENGTH: 22
<212> TYPE: DNA
<213> ORGANISM: Artificial
<220> FEATURE:
<223> OTHER INFORMATION: Primer

<400> SEQUENCE: 6
gaaggtgaag gtcggagtca ac                                            22

<210> SEQ ID NO 7
<211> LENGTH: 22
<212> TYPE: DNA
<213> ORGANISM: Artificial
<220> FEATURE:
<223> OTHER INFORMATION: Primer

<400> SEQUENCE: 7
cagagttaaa agcagccctg gt                                            22
```

COMPOSITIONS AND METHODS FOR INCREASING SODIUM CURRENT IN CARDIAC CELLS

CROSS-REFERENCE TO RELATED APPLICATION

This application is the § 371 U.S. National Stage of International Application No. PCT/US2021/027905, filed Apr. 19, 2021, which claims the benefit of U.S. Provisional Patent Application No. 63/012,351, filed Apr. 20, 2020, each of which is incorporated herein by reference in its entirety.

GOVERNMENT FUNDING

This invention was made with government support under HL104025 and HL106592 awarded by National Institutes of Health. The government has certain rights in the invention.

SUMMARY

This disclosure describes, in one aspect, a method of increasing sodium current in a cardiac cell. Generally, the method includes introducing into the cardiac cell an miR-448 inhibitor in an amount effective to decrease miR-448 suppression of SCN5A mRNA transcription, thereby increasing sodium current in the cardiac cell.

In another aspect, this disclosure describes a method of increasing translation of SCN5A mRNA in a cell. Generally, the method includes introducing into the cell an miR-448 inhibitor in an amount effective to decrease miR-448 suppression of SCN5A mRNA transcription.

In another aspect, this disclosure describes a method of decreasing arrythmia in a cardiac cell. Generally, the method includes introducing into the cardiac cell an miR-488 inhibitor in an amount effective to decrease miR-448 suppression of SCN5A mRNA transcription, thereby decreasing arrythmia in the cardiac cell.

In another aspect, this disclosure describes a method of treating arrythmia in a patient having, or at risk of having, arrythmia. Generally, the method includes administering to the patient an miR-448 inhibitor in an amount effective to decrease the likelihood or extent of arrythmia in the patient. In some embodiments, the patient has experienced myocardial infarction.

In some embodiments of all aspects, the miR-448 inhibitor can be an miR-448 antagomir or an miR-448 sponge.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

p<0.01 when compared between indicated groups by Student's t-test. (C) Effect of hypoxia on the miR-448 level in cardiomyocytes. Cells were incubated in normoxic (21% $O_2$) and hypoxic (2% $O_2$) conditions for six hours. (D) Effect of hypoxia-mimetic media on the miR-448 level in cardiomyocytes. RL14 cells were stimulated with cobalt chloride ($CoCl_2$) and deferoxamine (DFX) for 24 hours. Data are represented as the mean±standard deviation (SD) of three independent experiments. *p<0.001. In all cases, miR-448 level was detected by qPCR. The miRNA level was normalized with RNU6 level.

Figure 2:
Figure 2:
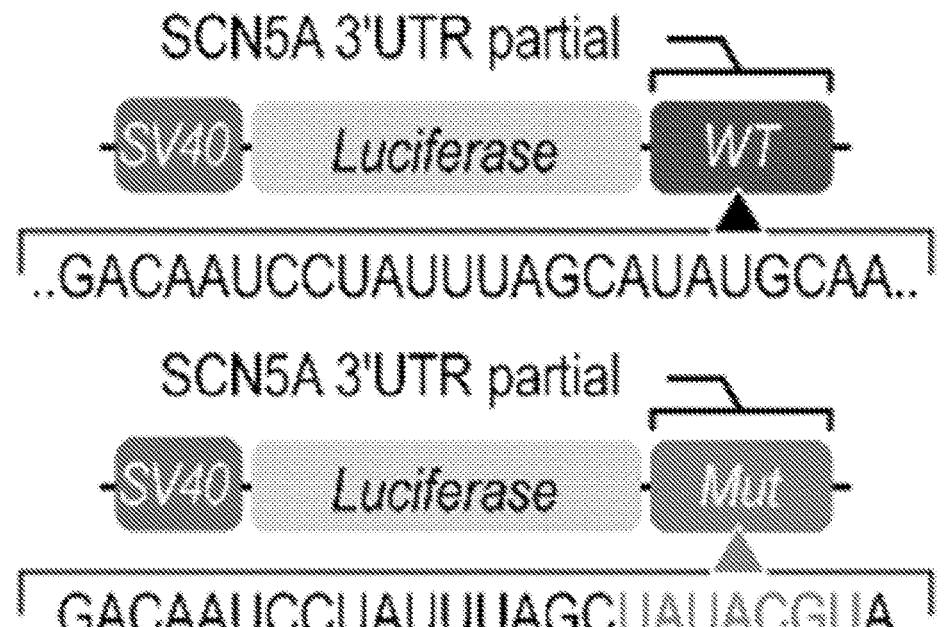

FIG. 2. SCN5A is a direct target of miR-448. (A) miR-448 sequence is shown (SEQ ID NO:1). Conserved miR-448 binding site within SCN5A 3'-UTR across seven species (SEQ ID NO:2). (B) Diagram of luciferase reporter constructs. The wild-type (WT, SEQ ID NO: 2) or mutant (Mut, SEQ ID NO:3) SCN5A 3'-UTR were inserted downstream of the luciferase gene of the pGL3-promoter vector.

Figure 3:
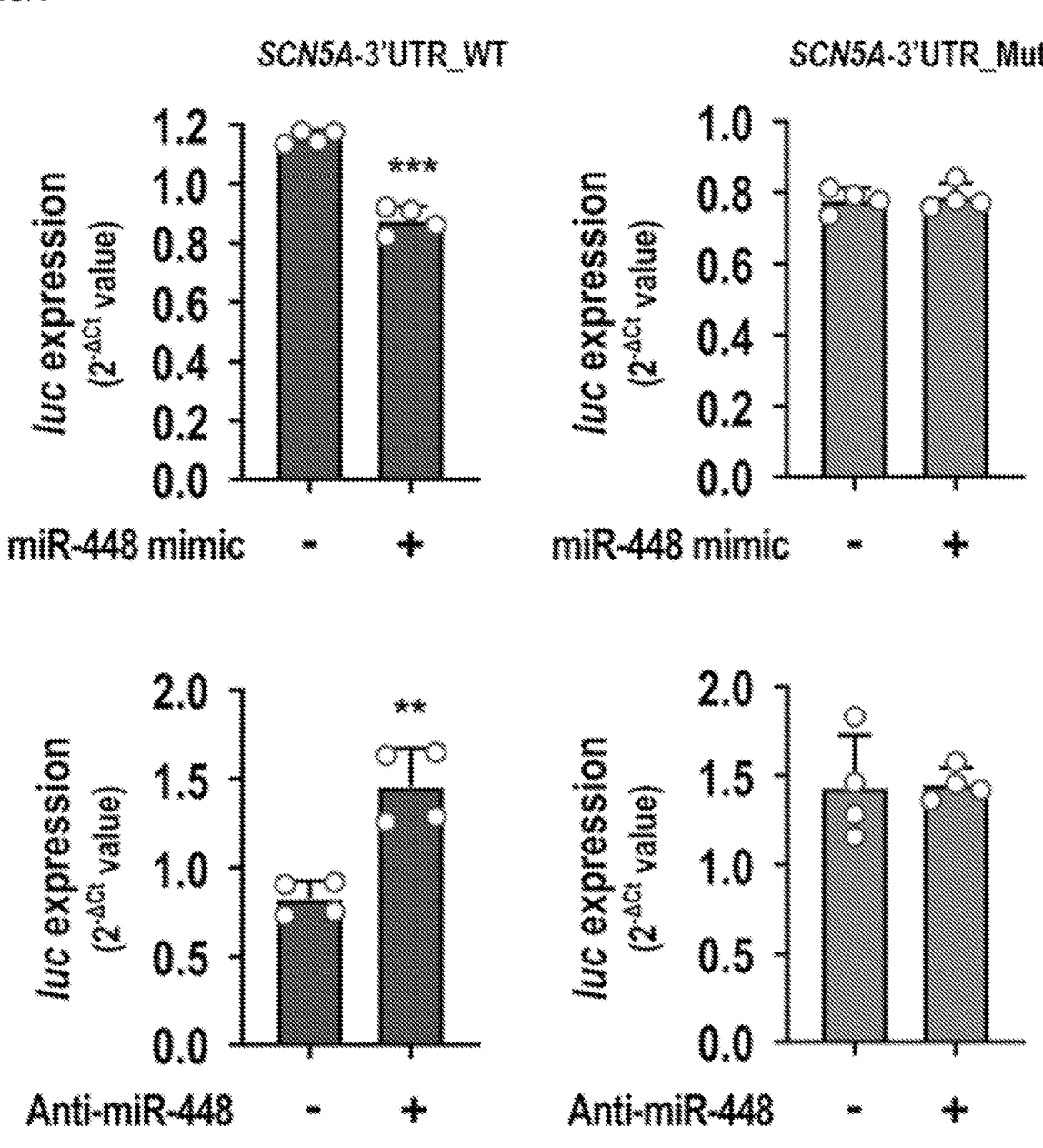

FIG. 3. Effect of miR-448 on the luciferase mRNA expression in human embryonic kidney 293T (HEK293T). Cells were transfected with wild type or mutation plasmid DNA, and then, miR-448 mimic or inhibitor were transfected into the cells (10 nM). SCN5A mRNA levels were detected by qPCR. The mRNA level of luciferase was normalized with the mRNA level of EGFP which was co-transfected for control. Data are shown as the mean+SD of four independent experiments. p<0.01, *p<0.001.

Figure 4:
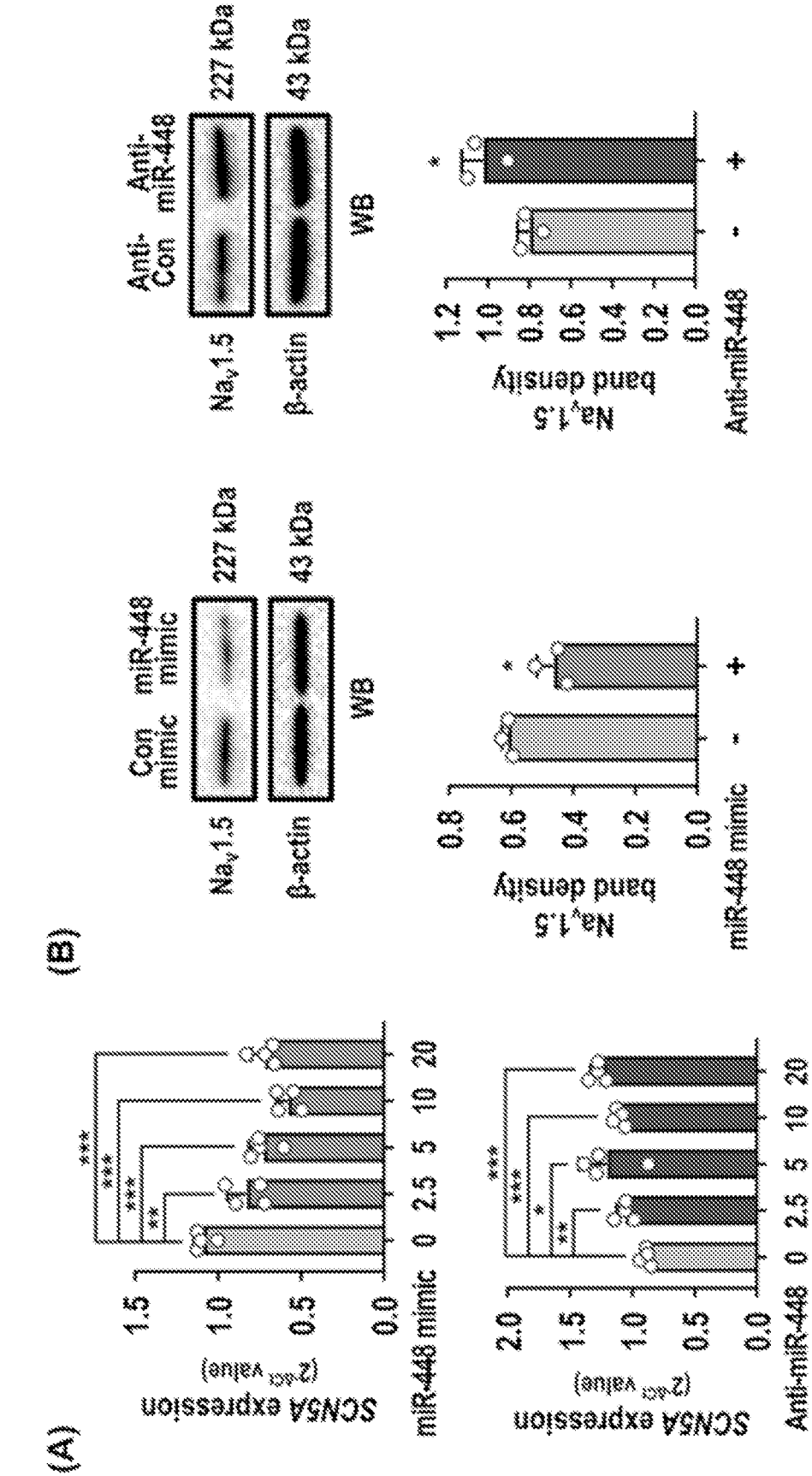

FIG. 4. SCN5A is regulated by miR-448. (A) Effect of miR-448 on the SCN5A mRNA level in cardiomyocytes. Cells were transfected with mimic or anti-miR-448 (2.5 nM, 5 nM, 10 nM, or 20 nM) and then incubated for 24 hours. After RNA preparation and cDNA synthesis, SCN5A mRNA level was detected by qPCR. The mRNA level of SCN5A was normalized with GAPDH mRNA level. (B) Effect of miR-448 on the protein level of SCN5A in cardiomyocytes. Cells were transfected with mimic or anti-miR-448 (10 nM) and then incubated for 24 hours. After protein isolation, $Na_v1.5$ protein level was detected by Western blotting (top). Band density was normalized with 3-actin from three independent experiments and quantified (bottom). Data are represented as the mean+standard deviation (SD) of three independent experiments. One-way ANOVA with Sidak's multiple comparisons test was performed to determine the p-value. *p<0.05, p<0.01, *p<0.001.

Figure 5:
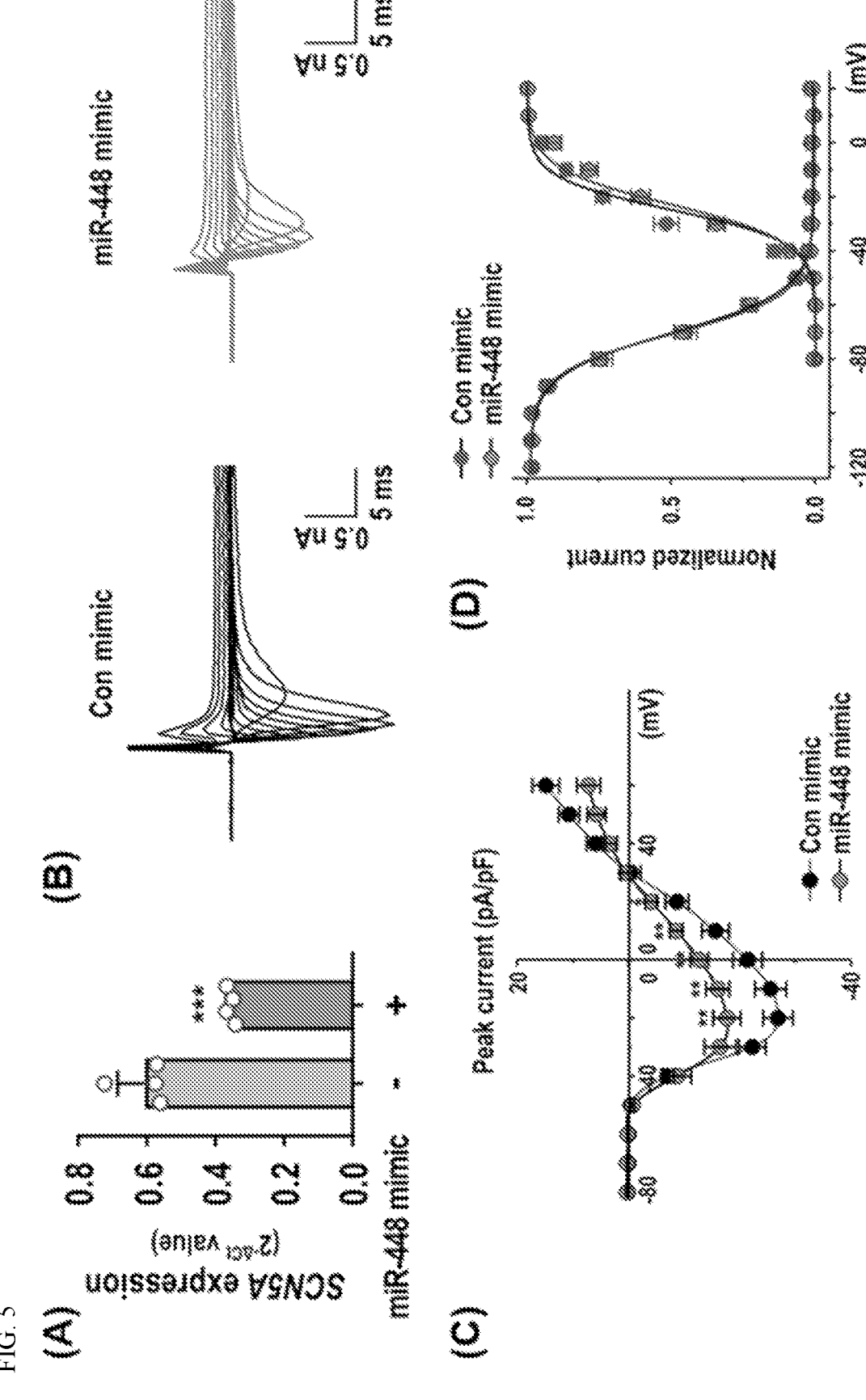

FIG. 5. Sodium channel currents are reduced by miR-448 mimic in iPSC-cardiomyocytes. (A) Effect of miR-448 mimic on the mRNA level of SCN5A in iPSC-cardiomyocytes (CMs). The cells were transfected with miR-448 mimic (10 nM) and then incubated for 24 hours. The mRNA level of SCN5A was normalized with GAPDH mRNA level. (B) Representative whole-cell sodium current traces in response to increasing step depolarizations from either control (left) or miR-448 mimic-transfected iPSC-CMs (right). (C) Average sodium current-voltage relationship of voltage-dependent sodium channels from either control (black) or miR-448 mimic (red)-transfected iPSC-CMs. (D) Average voltage-dependence of activation and steady-state inactivation in control (black) and miR-448 mimic-transfected iPSC-CMs (red). For the activation curve, normalized peak conductance was plotted as a function of the membrane potential. For the inactivation curve, peak sodium currents were normalized to maximum values in each cell and plotted as a function of the voltage of the conditioning step. Data are represented as the mean+standard deviation (SD) or ±standard error (SE). *p<0.05, **p<0.01.

Figure 6:
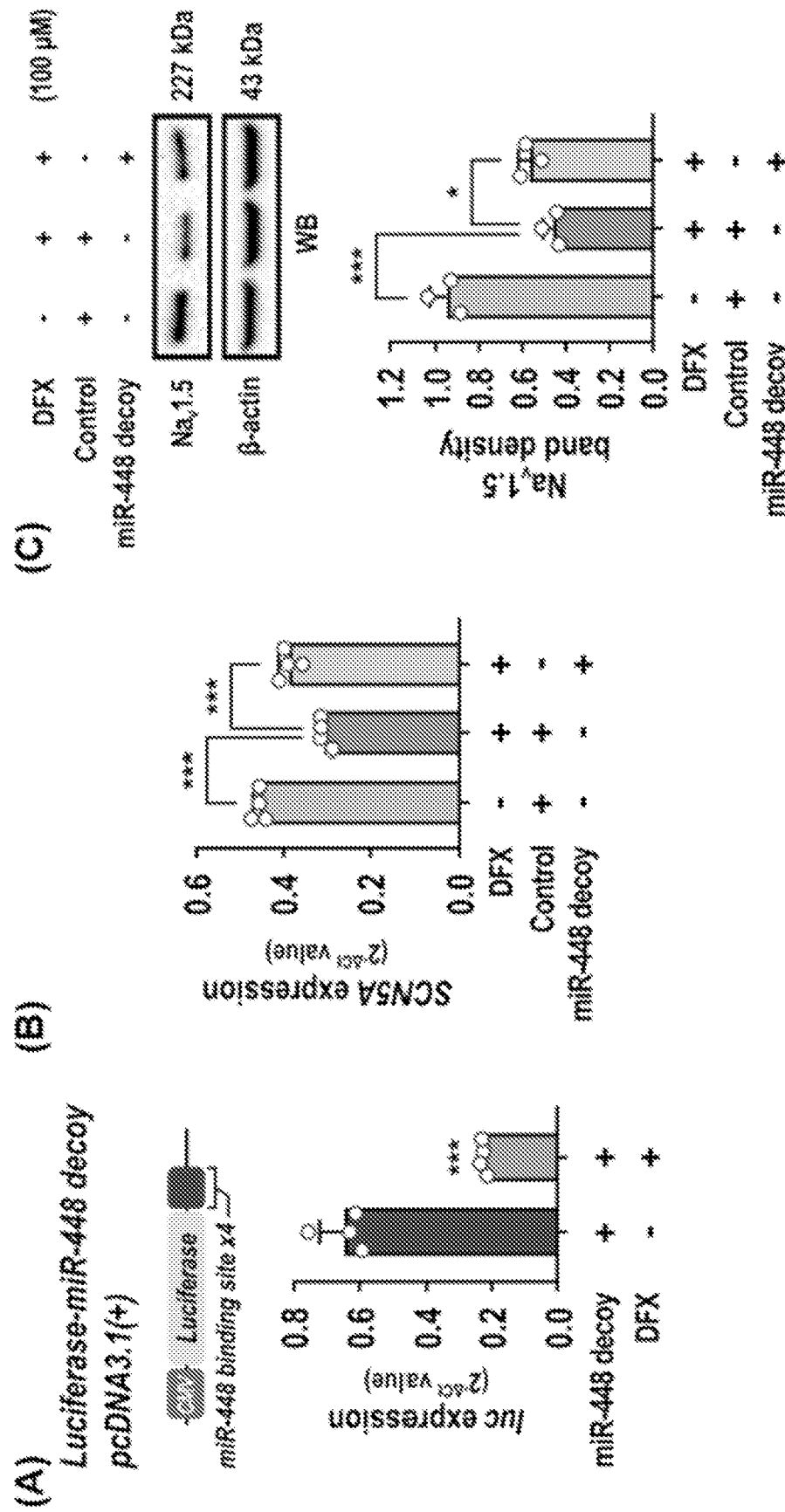

FIG. 6. SCN5A is regulated by hypoxia-induced miR-448. (A) Diagram of luciferase reporter constructs. The miR-448 binding sequences were inserted downstream of the luciferase gene of the pGL3-promoter vector. Cells were transfected with miR-448 decoy and then the expression of LUC was checked in a presence or absence of deferoxamine (DFX). (B) Effect of miR-448 decoy on the expression of SCN5A mRNA reduced by deferoxamine in cardiomyocytes. Cells were transfected with miR-448 decoy and then stimulated with deferoxamine for six hours. The mRNA level of SCN5A was normalized with GAPDH mRNA level. (C) Effect of miR-448 decoy on the deferoxamine-induced $Na_v1.5$ protein in cardiomyocytes. Cells were transfected with miR-448 decoy and then stimulated with deferoxamine for 24 hours. After protein isolation, $Na_v1.5$ protein level was detected by Western blotting (top) and quantified (bottom). Band density was normalized with 3-actin from three independent experiments. Data are represented as the mean+ standard deviation (SD) of three independent experiments. *p<0.05, ***p<0.001.

Figure 7:
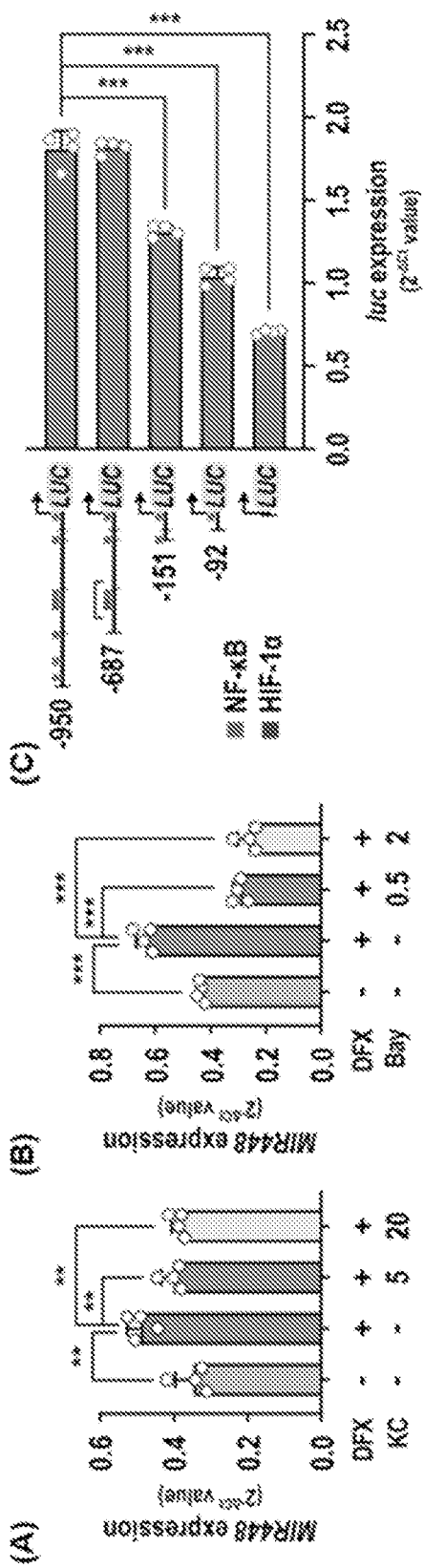

FIG. 7. HIF1α and NF-κB are upregulators of MIR448 in hypoxia. (A) Effect of KC7F2, an HIF1α inhibitor, on the induction of miR-448 by deferoxamine in cardiomyocytes. The cells were treated with HIF1α inhibitor of NF-κB inhibitor in a dose-dependent manner (5 μM or 20 μM) for 30 minutes and then were stimulated with deferoxamine for six hours. The miRNA level was normalized with RNU6 level. (B) Effect of Bay11-7082, an NF-κB inhibitor, on the induction of miR-448 by deferoxamine in cardiomyocytes. The cells were treated with HIF1α or Bay11-7082 in a dose-dependent manner (0.5 μM or 2 μM) for 30 minutes and then were stimulated with deferoxamine for six hours. The miRNA level was normalized with RNU6 level. (C) Predicted binding sites for HIF1α and NF-κB are within 1 Kb upstream of the MIR448 transcriptional initiation site. Diagrams show luciferase reporter constructs with 1 Kb promoter MIR448 region or series of deletion mutants. Each DNA construct was transfected into cardiomyocytes, and the cells were stimulated with deferoxamine for six hours. Luciferase mRNA level was detected by qPCR. The mRNA level of luciferase was normalized with the mRNA level of EGFP which was co-transfected as a control. Data are represented as the mean+standard deviation (SD) of three independent experiments. p<0.01, *p<0.001.

Figure 8:
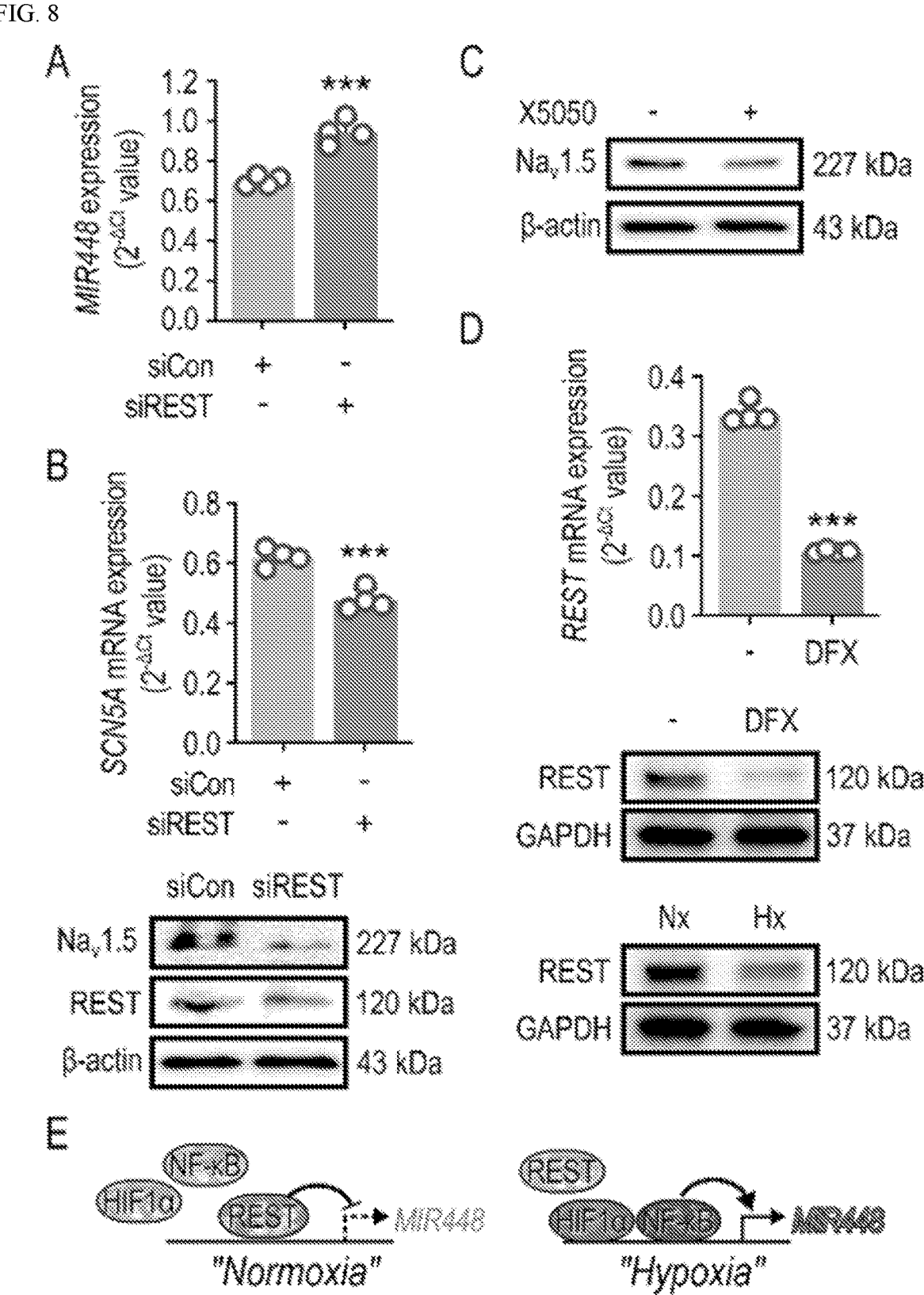

FIG. 8. Ischemia relieves REST repression of MIR-448. (A) Effect of REST gene silencing on the miR-448 level in cardiomyocytes. The cells were transfected with control or REST siRNA for 24 hours. After RNA preparation and cDNA synthesis for miRNA, mature miR-448 level was detected by qPCR. The miRNA level was normalized with RNU6 level. (B) Effect of REST gene silencing on the mRNA (top) and protein level (bottom) of SCN5A in cardiomyocytes. The cells were transfected with control or REST siRNA for 24 hours. SCN5A mRNA level was detected by qPCR. The mRNA level of SCN5A was normalized with GAPDH mRNA level. After protein isolation, $Na_v1.5$ protein level was detected by Western blotting. (C) Effect of X5050, a REST inhibitor, on the protein level of $Na_v1.5$ in cardiomyocytes. The cells were treated with X5050 for 24 hours. After protein isolation, $Na_v1.5$ protein level was detected by Western blotting. (D) Effect of hypoxic condition on the mRNA (top) and protein level (bottom) of REST. The cardiomyocytes were stimulated with deferoxamine for six hours or were incubated with normoxia or hypoxia for six hours. The mRNA level of REST was normalized with GAPDH mRNA level. After protein isolation, REST protein level was detected by Western blotting. (E) Diagram showing MIR-448 transcriptional regulation by HIF1α, NF-κB, and REST in normoxia and hypoxia. Data are represented as the mean+standard deviation (SD) of three independent experiments. ***p<0.001.

Figure 9:
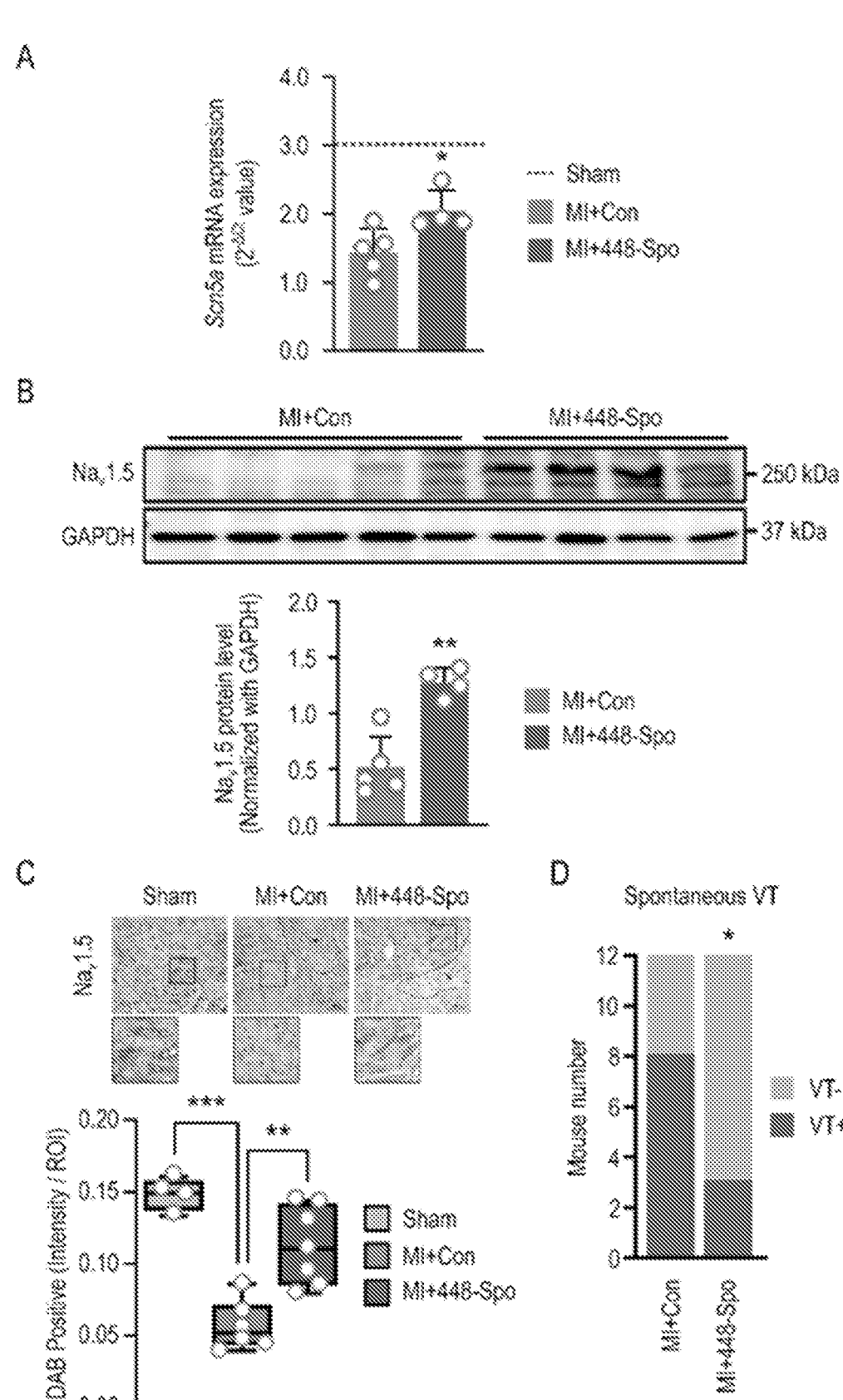

FIG. 9. Blocking miR-448 improves $Na_v1.5$ levels and arrhythmic risk after myocardial infarction. (A) Effect of miR-448 antagonism on cardiac SCN5A mRNA level after myocardial infarction. The heart tissues were collected from MI+Con or MI+448-Spo. (B) Effect of miR-448 antagonism on protein level of cardiac $Na_v1.5$ after myocardial infarction. The heart tissues were collected from MI+Con or MI+448-Spo. (C) Immunohistochemical (IHC) localization of $Na_v1.5$ antigen done using formalin-fixed, paraffin-embedded heart tissues. Tissue sections were incubated with $Na_v1.5$ antibody. Positively stained cells were evaluated using Image J analysis. (D) The number of mice in each group with or without ventricular tachycardia (VT). Data are represented as the mean+ or ±standard deviation (SD). *p<0.05, p<0.01, *p<0.001.

Figure 10:
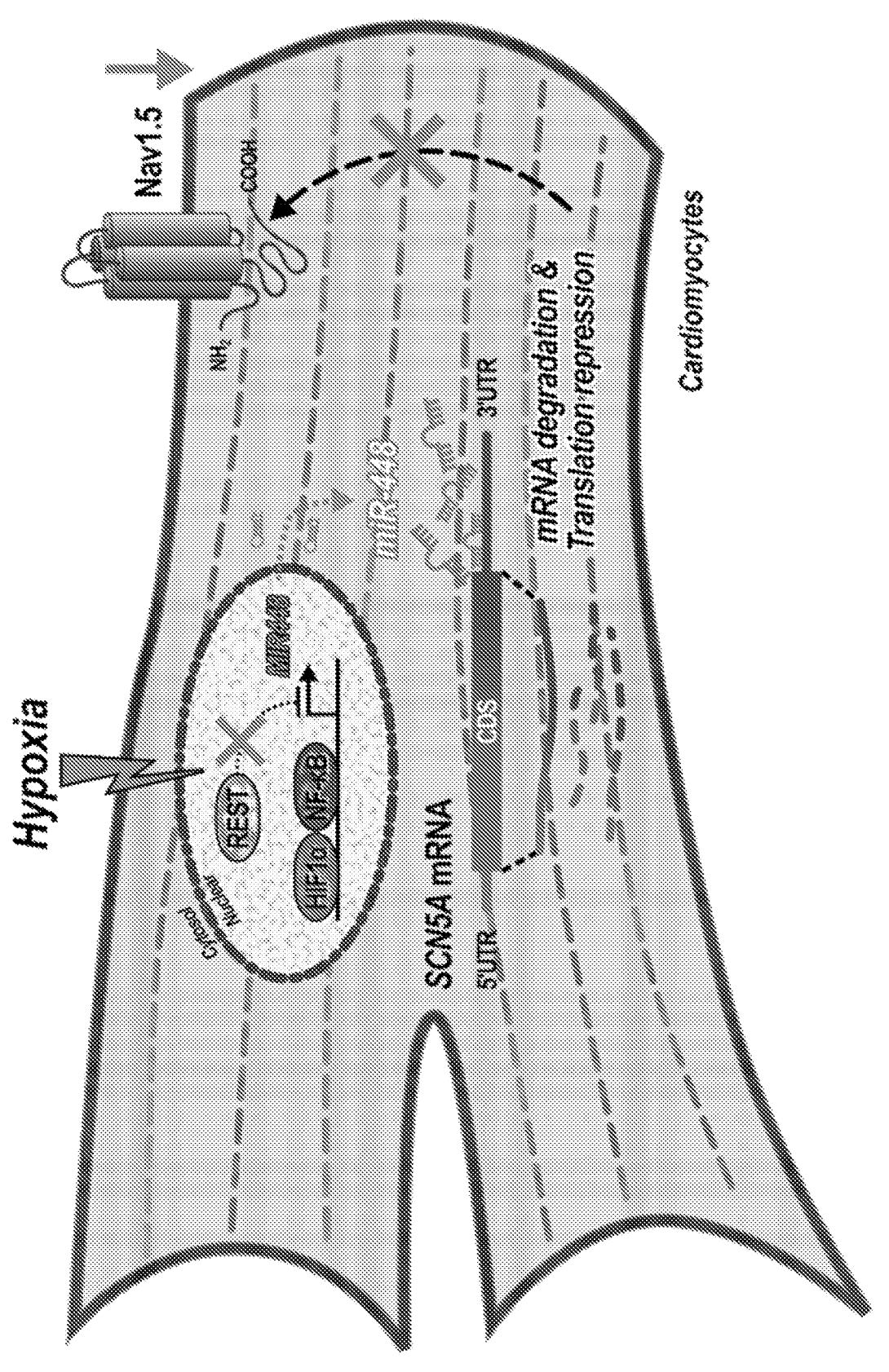

FIG. 10. Summary of the effect of hypoxia on miR-448, SCN5A and arrhythmic risk.

Figure 11:
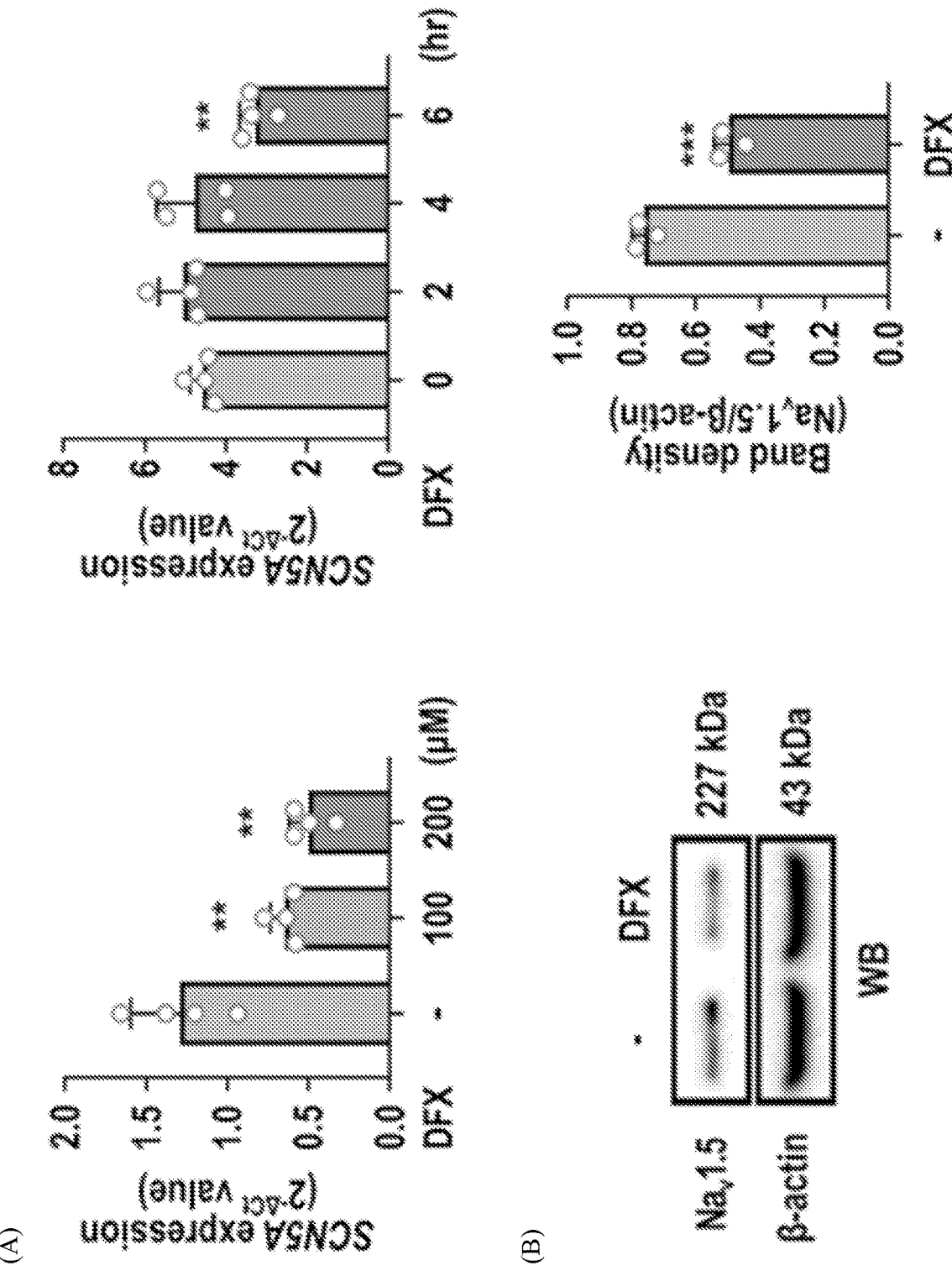

FIG. 11. Effect of deferoxamine (DFX) on the expression of SCN5A in RL14 human cardiomyocytes. (A) Effect of deferoxamine on the SCN5A mRNA level in cardiomyocytes. Cells were stimulated with deferoxamine in a dose-dependent (left) or time-dependent (right) manner. (B) Effect of deferoxamine on the protein level of SCN5A in cardiomyocytes. Cells were stimulated with deferoxamine (100 μM) for 24 hours. Data are represented as the mean+ standard deviation (SD) of three to four independent experiments. p<0.01, *p<0.001

Figure 12:
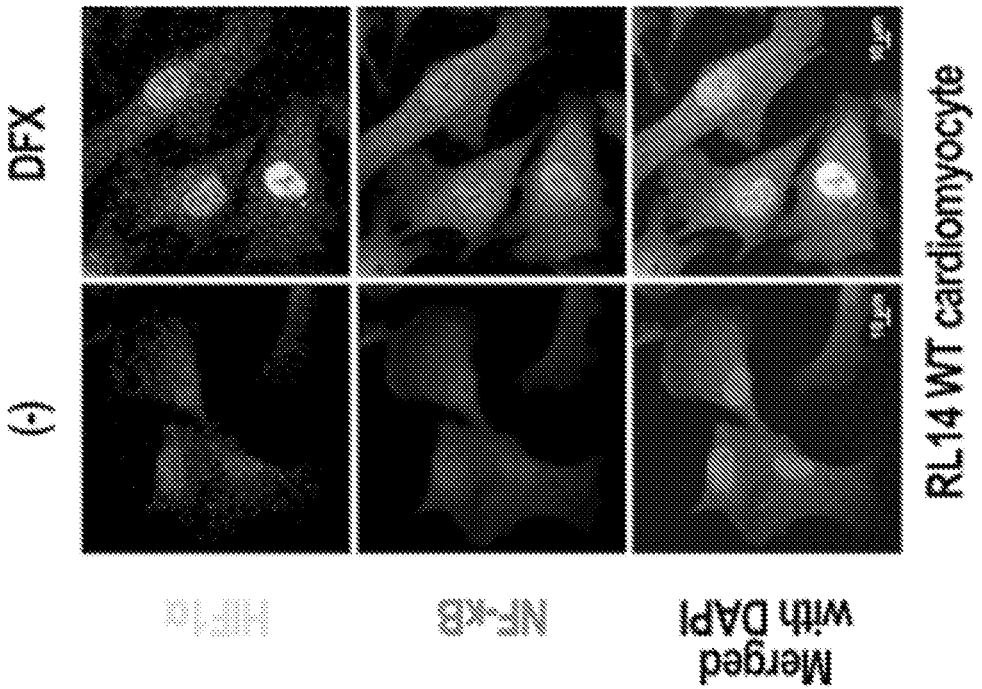
Figure 12:
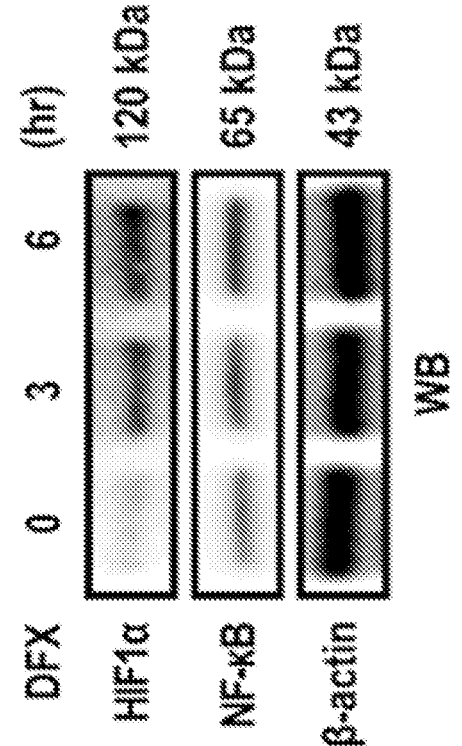

FIG. 12. Effect of deferoxamine on the expression and translocation of HIF1α and NF-κB. Effect of deferoxamine on the HIF1α and NF-κB in RL14 cells. Cells were stimulated with deferoxamine for six hours. The expression and nuclear translocation of HIF1α and NF-κB was determined using Western blotting and confocal microscopy.

Figure 13:
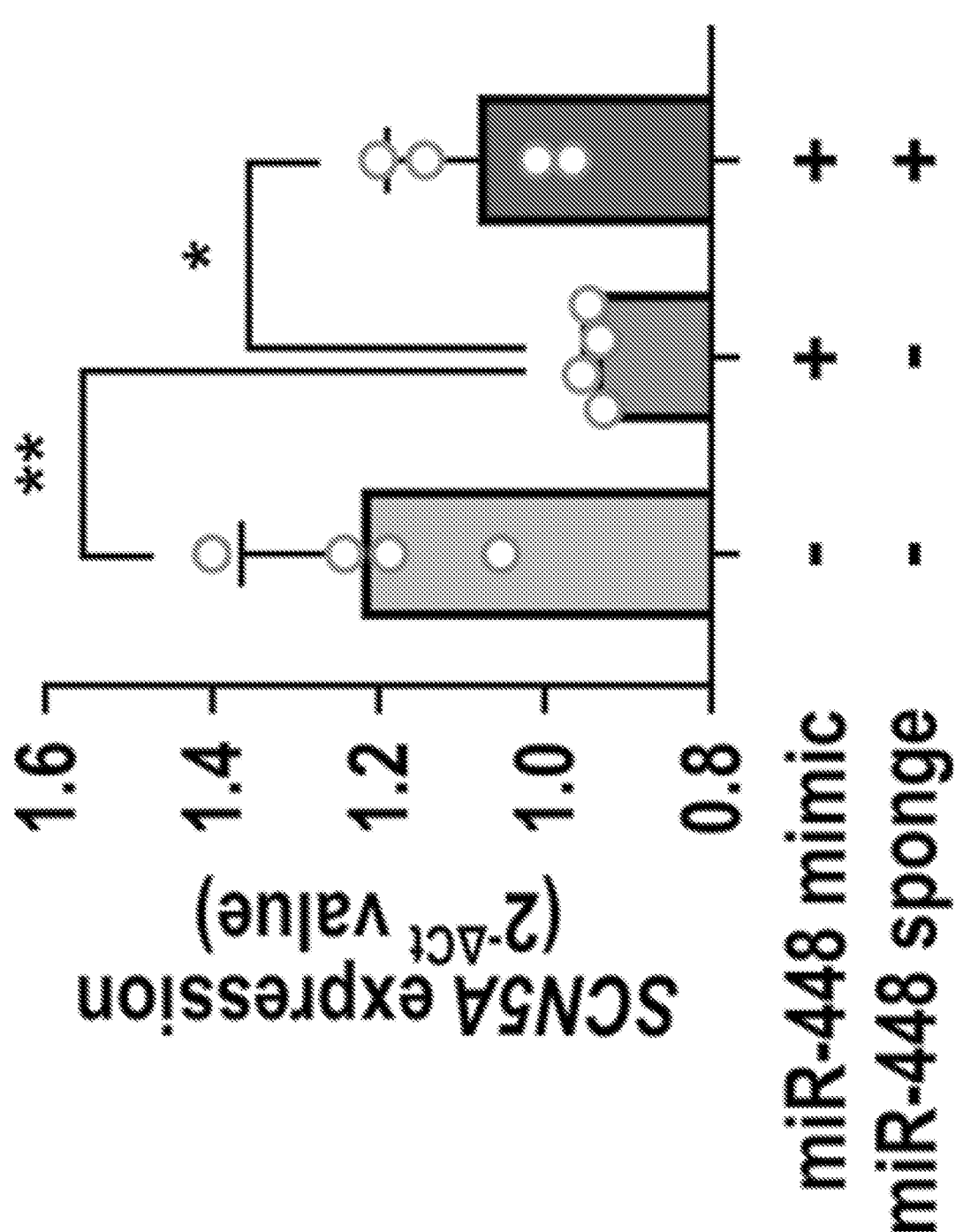

FIG. 13. Effect of miR-448 sponge on miR-448 mimic-mediated reduction of SCN5A. Effect of miR-448 sponge on the expression of SCN5A mRNA reduced by miR-448 mimic in cardiomyocytes. Cells were transfected with miR-448 mimic in a presence or absence of miR-448 sponge. Data are represented as the mean+standard deviation (SD) of four independent experiments. *p<0.05, **p<0.01.

Figure 14:
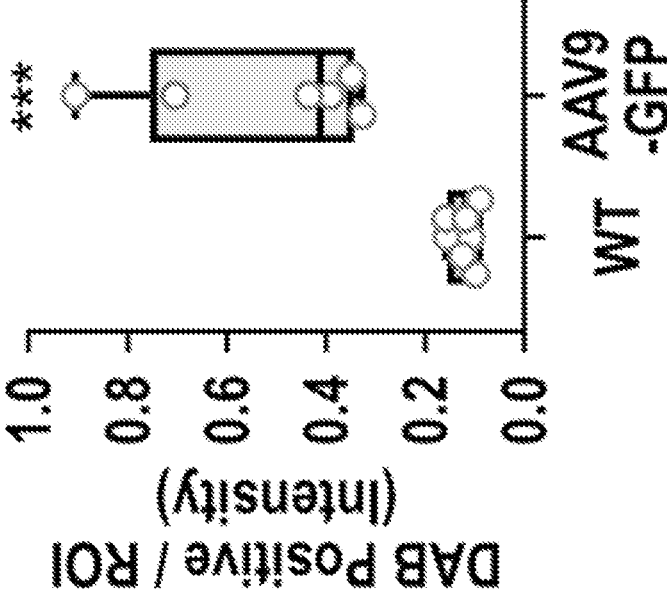
Figure 14:
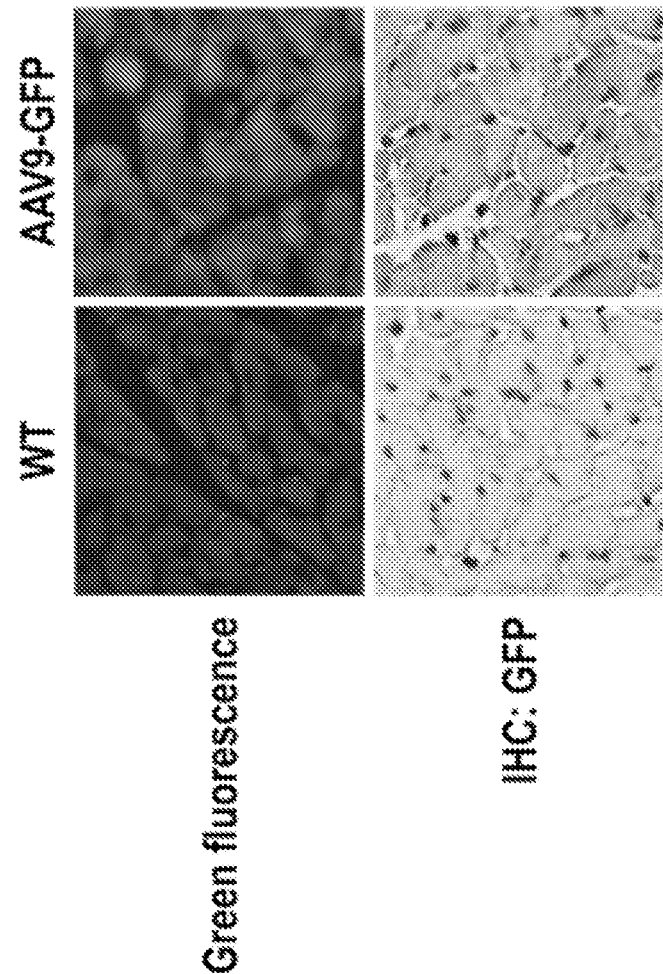

FIG. 14. GFP expression by AAV9 in mouse heart tissue. AAV9 particles expressing GFP were injected intravenously. After two weeks, green fluorescence was determined using fluorescence microscopy. Immunohistochemistry of GFP antigen was done using formalin-fixed, paraffin-embedded heart tissues. Tissue sections were incubated with GFP antibody. Positively stained cells were evaluated using Image J analysis. Data are represented as the mean±standard deviation (SD). ***, P<0.001.

Figure 15:
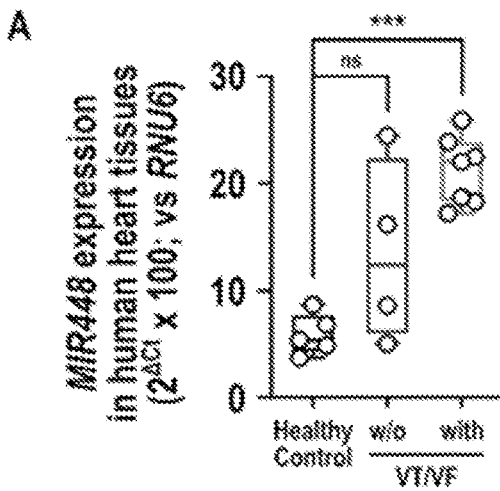
Figure 15:
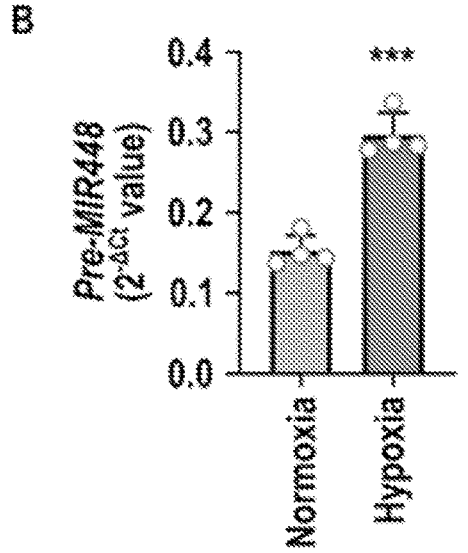
Figure 15:
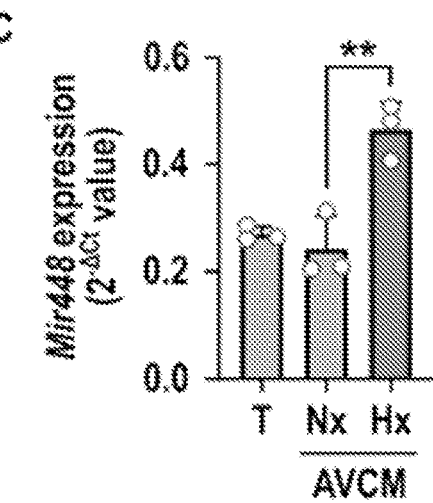
Figure 15:
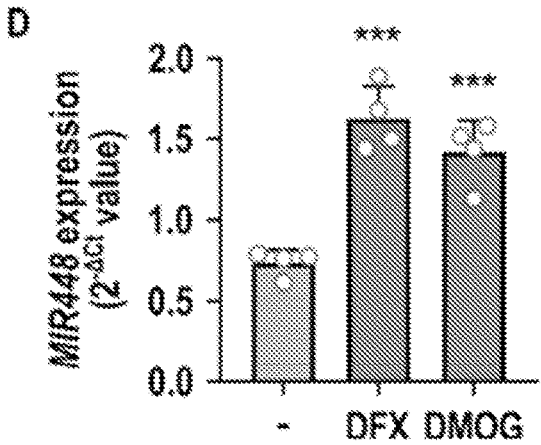

FIG. 15. Effect of hypoxic condition on the expression miR-448. (A) Expression of miR-448 in the left ventricle of controls or human heart failure patients with or without ventricular tachycardia or ventricular fibrillation. Using tissues obtained from a tissue bank, 11 patients had cardiomyopathy and whose arrhythmia status was documented in the records. Seven patients had documented ventricular tachycardia or ventricular fibrillation. When comparing these patients to controls, there was a statistically significant increase in miR-448 in the left ventricle. miR-448 levels showed a trend of increasing as a function of arrhythmic risk. (B) Effect of hypoxia on the precursor miR-448 level in cardiomyocytes. RL14 cells were incubated in normoxic (21% $O_2$) and hypoxic (2% $O_2$) conditions for six hours. (C) Effect of hypoxia on the miR-448 level in the isolated mouse adult ventricular cardiomyocytes (AVCM). AVCMs were incubated in normoxic (21% $O_2$; Nx) and hypoxic (2% $O_2$; Hx) conditions for 24 hours. T: acutely isolated control hearts. (D) Effect of hypoxia-mimetic media on the miR-448 level in cardiomyocytes. RL14 cells were stimulated with deferoxamine (DFX) and dimethyloxalylglycine (DMOG) for 24 hours. Data are represented as the mean+standard deviation (SD) of four independent experiments. \*\*p<0.01, \*\*\*p<0.001.

Figure 16:
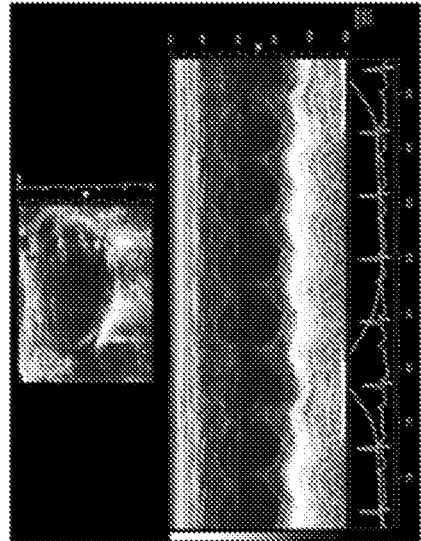
Figure 16:
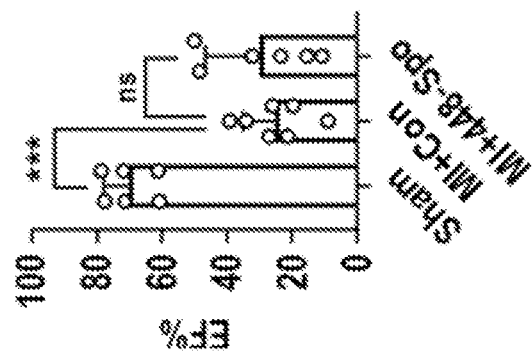

FIG. 16. Echocardiogram analysis in mice with AAV9-Con and AAV9-448-Spo. (Top) Representative mouse M-mode echocardiography images of the mice in each group. (Bottom) Measurements of the ejection fraction (EF), n=6-7/group. Data are represented as the mean+standard deviation (SD). \*\*\*p<0.001.

Figure 17:
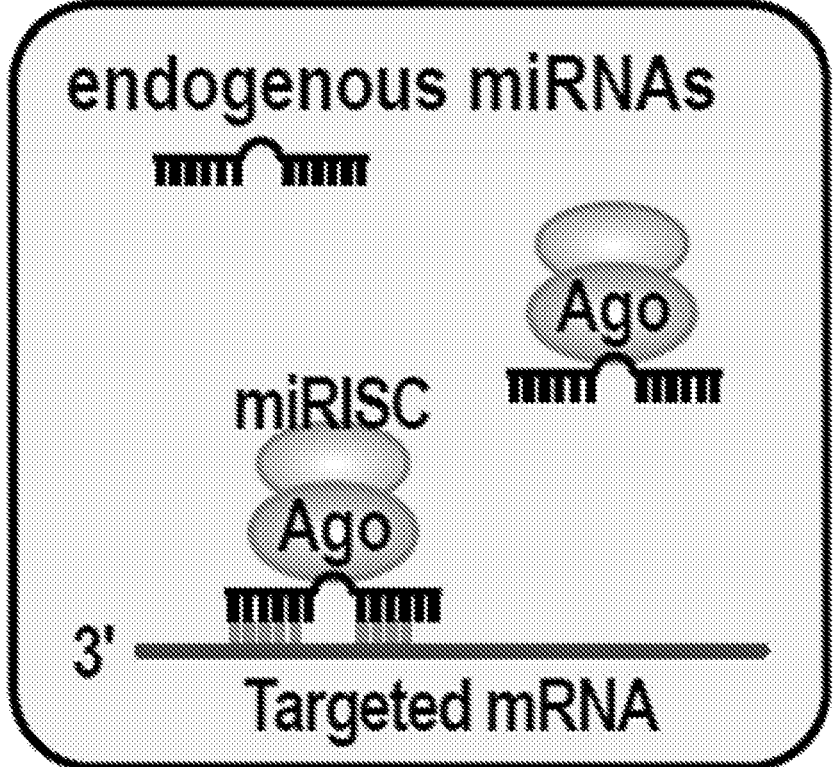

FIG. 17. Normal endogenous mRNA regulation involving miRNAs. Endogenous miRNAs are involved in normal mRNA degradation, which represses synthesis of protein encoded by the mRNA being degraded.

Figure 18:
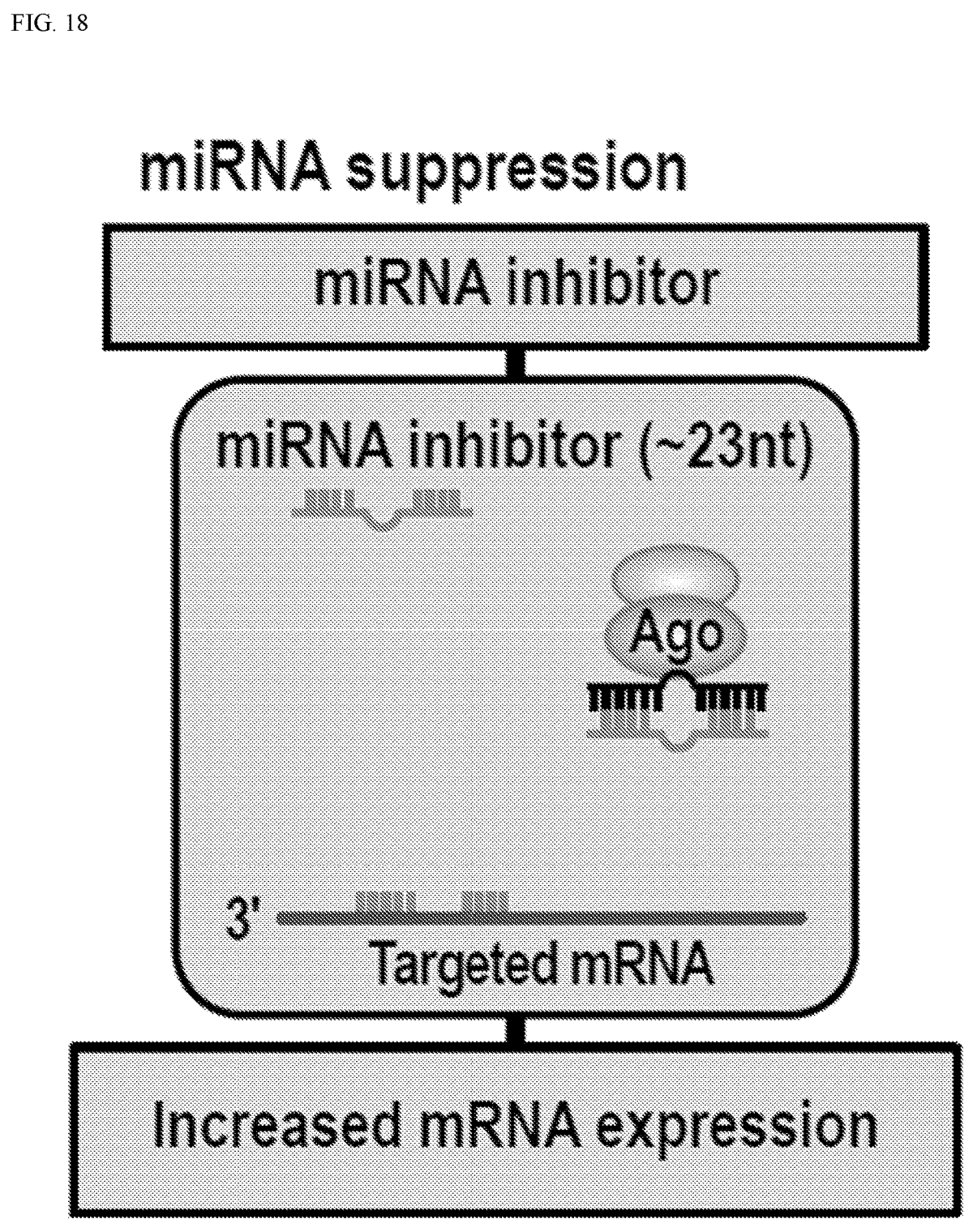

FIG. 18. Inhibition of endogenous miRNA regulation promotes protein expression. The miRNA inhibitor interferes with the ability of miRNA to degrade mRNA so that the mRNA remains available for protein translation.

Figure 19:
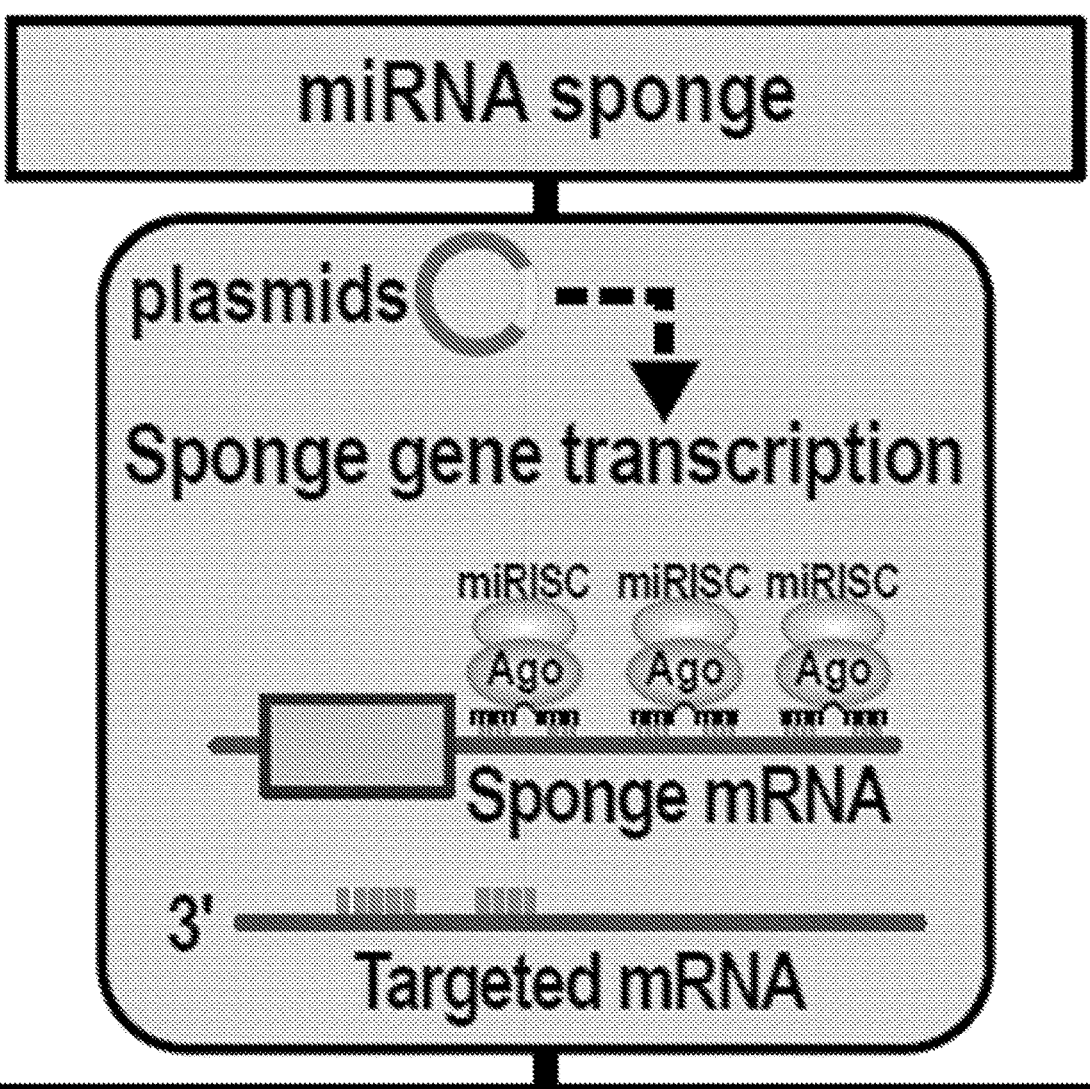

FIG. 19. An miRNA sponge inhibits endogenous miRNA regulation of protein expression. An miRNA sponge is an mRNA that contains binding sites complementary to an miRNA of interest. The miRNA sponge sequesters miRNA complexes so that the mRNA remains available for protein translation.

Figure 20:
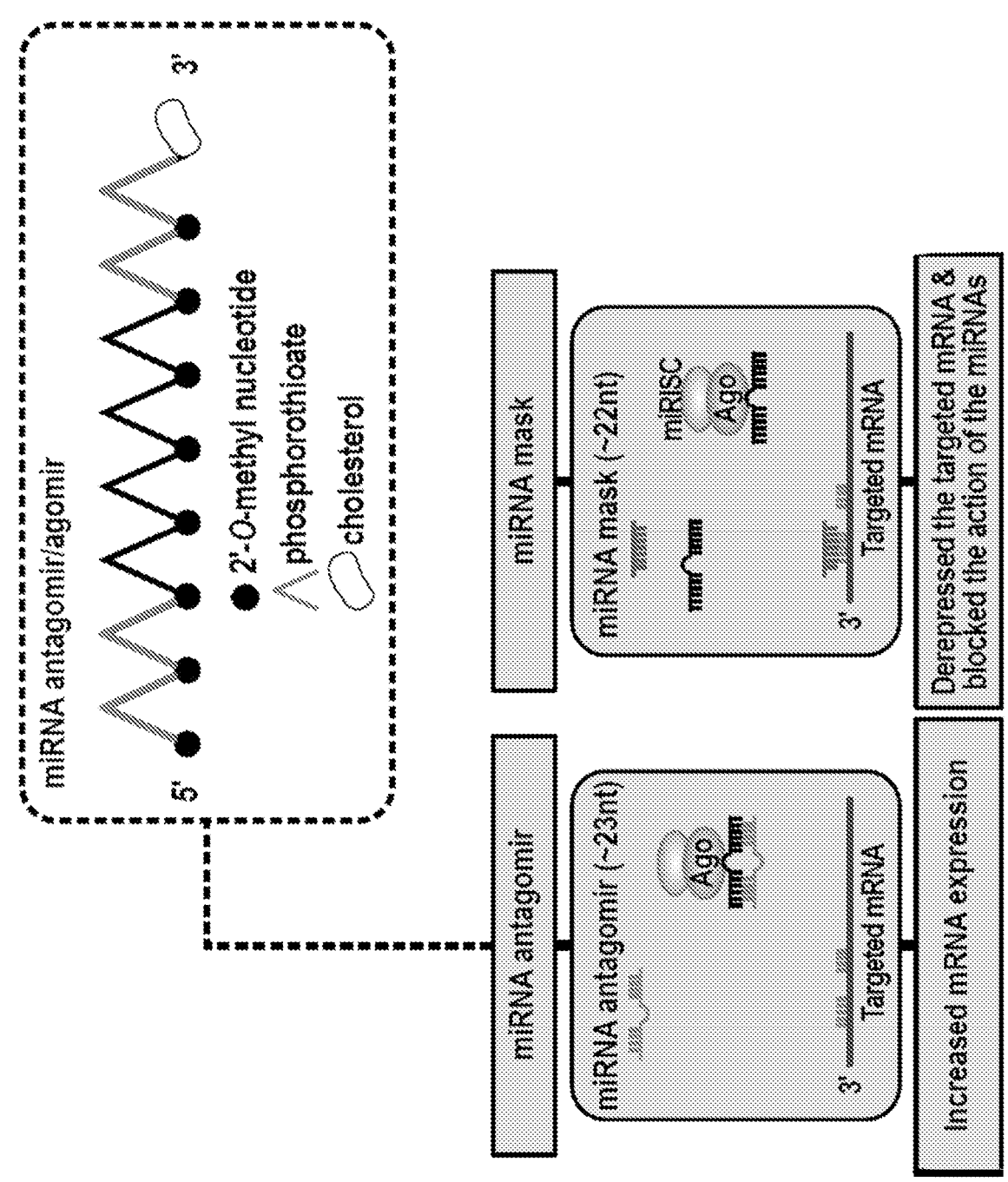

FIG. 20. An miRNA antagomir or miRNA mask inhibits endogenous miRNA regulation of protein expression. An miRNA antagomir is a chemically engineered oligonucleotide that interferes with other molecules from binding to a desired site on an mRNA molecule. Antagomirs are used to silence endogenous microRNA (miR). An antagomir is complementary to the specific miRNA target with either mispairing at the cleavage site of Ago2 or some sort of base modification to inhibit Ago2 cleavage. For example, an antagomir can be modified to possess a 2-methoxy group and/or phosphorothioate, and/or cholesterol to make them more resistant to degradation. An miRNA mask is complementary to the portion of an mRNA to which an miRNA binds, thereby derepressing translation of the mRNA by blocking access of the miRNA to the mRNA.

DETAILED DESCRIPTION OF ILLUSTRATIVE EMBODIMENTS

This disclosure describes compositions and methods that improve the ability of cells to make and use proteins that allow the cells to conduct a sodium current across the cell membrane. In a clinical setting, the methods may be useful to improve the function of cardiac cells and decrease the likelihood and/or extent of arrhythmia that can occur, for example, following myocardial infarction.

Cardiac ischemia is associated with arrhythmic risk, but effective therapies are limited. The cardiac voltage-gated sodium channel α-subunit (SCN5A) coding region encodes the $Na_v1.5$ channel subunit. $Na_v1.5$ channels mediate sodium current in cardiac cells. Ischemic cardiomyopathy is associated with reduced $Na_v1.5$, and reduced $Na_v1.5$ contributes to arrhythmic risk. This disclosure shows that hypoxia reduces $Na_v1.5$ through effects on a microRNA (miR), miR-448. The expression of miR-448 is increased in ischemic cardiomyopathy. miR-448 has a conserved binding site in the 3'-UTR of SCN5A. miR-448 binding to this site suppresses SCN5A expression and sodium currents. Hypoxia-induced HIF1α and NF-κB are transcriptional regulators for MIR448. Hypoxia also relieved MIR448 transcriptional suppression by RE1 silencing transcription factor (REST). Inhibition of miR-448 reduced arrhythmic risk after myocardial infarction. These results indicate that ischemia drives miR-448 expression, reduced $Na_v1.5$ current, and increases risk of arrhythmic. Arrhythmic risk is reduced by inhibiting $Na_v1.5$ downregulation, suggesting a new approach to antiarrhythmic therapy.

Regulation of $Na_v1.5$ expression depends on equilibrium between different stages of protein expression: e.g., gene transcription, RNA processing, post-transcriptional regulation by miRNA or RNA binding proteins, protein synthesis, protein assembly, post-translational modification, and protein trafficking. Cardiac sodium channel downregulation can therefore be mediated by transcriptional regulation, post-transcriptional mRNA splicing, modulation of mRNA stability, translational regulation, and post-translational modification. However, the mechanism through which ischemia causes $Na_v1.5$ downregulation has been unclear. This disclosure reports that miR-448 is upregulated in cardiac ischemia and contributes to the downregulation of $Na_v1.5$. miR-448 is a microRNA. MicroRNAs (miRNAs) are small (20~22 nucleotides) non-coding RNA molecules that function in RNA silencing and post-transcriptional regulation of gene expression.

miR-448 is Upregulated with Cardiac Ischemia

Figure 1:
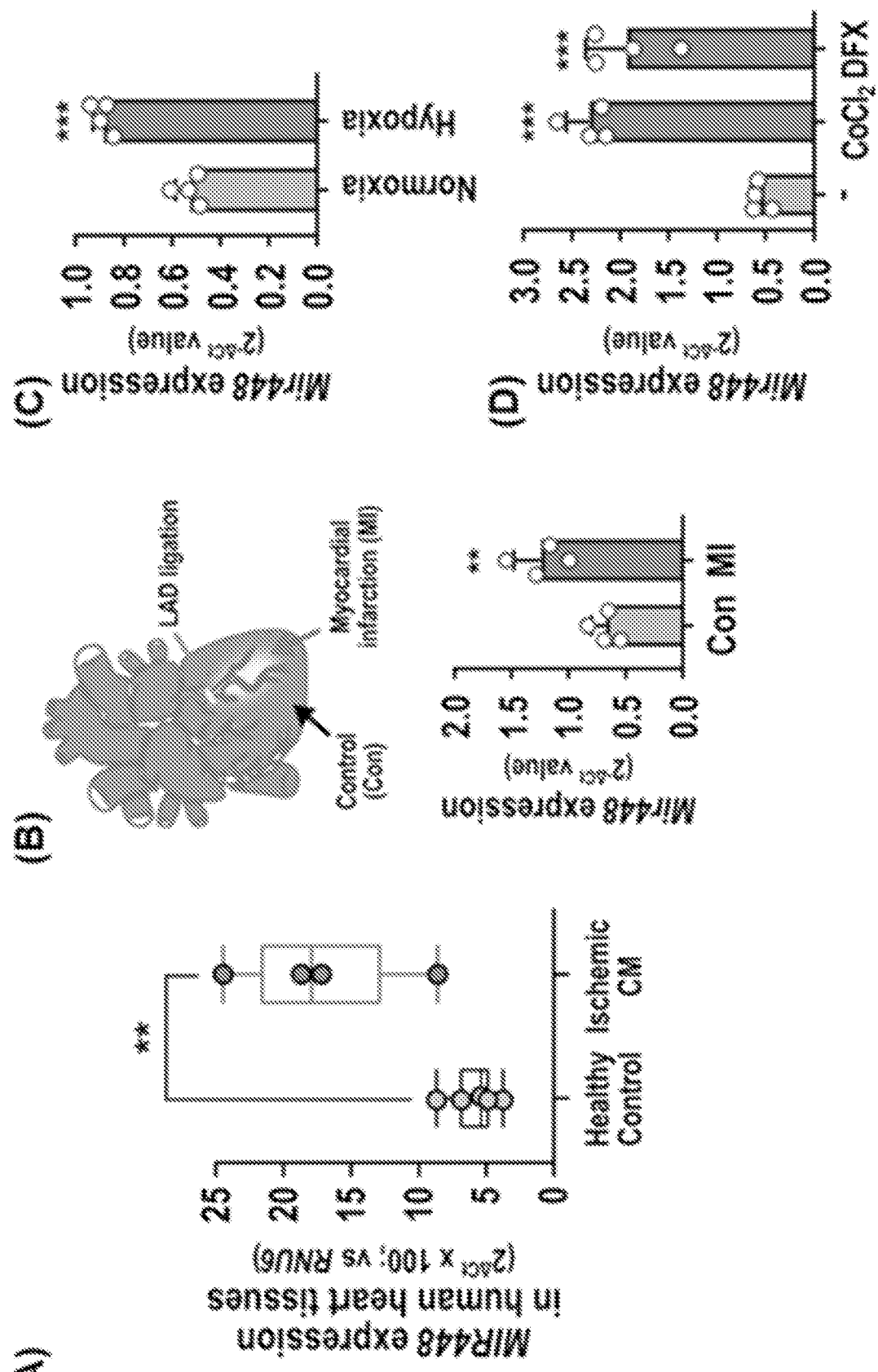
FIG. 1. miR-448 increases in ischemia. (A) Expression of miR-448 in human ischemic cardiomyopathy. Left ventricle tissue was obtained from heart failure patients with ischemic cardiomyopathy. Healthy control n=5, Ischemic CM n=4. (B) Expression of miR-448 in murine myocardial infarction. Left ventricle tissue was obtained from the peri-infarct and distal regions for comparison. Data are represented as the mean± or +standard deviation (SD) of four to five samples.

Cardiac miR-448 expression was significantly increased in heart tissues from patients with ischemic cardiomyopathy compared to healthy controls. miR-448 level scaled with arrhythmic risk (FIG. 15A). A similar upregulation was noted in mouse heart tissue taken from the myocardial infarction border region when compared to the control remote region (FIGS. 1A and 1B). RL14 human cardiomyocytes were used to confirm hypoxia could increase miR-448. Compared with normoxia (21% $O_2$), incubating with hypoxia (2% $O_2$) for six hours caused an increase in the levels of both the mature and precursor form of miR-448 (FIG. 1C, FIG. 15B). Normoxic levels of miR-448 were comparable to those obtained in vivo under control conditions, and similar changes in miR-448 in response to changes in $O_2$ tension were noted in acutely isolated adult cardiomyocytes (FIG. 15C). miR-448 expression was also increased by the hypoxia-mimetic chemicals, cobalt chloride ($CoCl_2$), deferoxamine (DFX), and dimethyloxallyl glycine (DMOG) (FIG. 1D, FIG. 15D).

SCN5A is a Direct Target of miR-448

Sequence analysis revealed a complementary binding sequence for miR-448 within the 3'-UTR of SCN5A mRNA. This binding site is highly conserved in many mammals including human and mouse (FIG. 2A). Wild-type (WT) or DNA constructs with a mutation of the binding site for miR-448 in 3-UTR of SCN5A were used to confirm SCN5A as a target of miR-448. The DNA construct carried the SV40 promoter, placed in control of a luciferase coding region and a partial SCN5A 3'-UTR that contained WT or mutant sequences for the miR-448 consensus binding site (FIG. 2B). Therefore, if miR-448 bound to and regulated the SCN5A 3'-UTR site, expression of luciferase would also be regulated concomitantly. EGFP-expressing DNA was transfected together with the SCN5A 3'-UTR construct, and EGFP was used as an expression control. Luciferase mRNA levels were decreased by the miR-448 mimic (FIG. 3, upper left pane) and increased by the miR-448 inhibitor (FIG. 3, lower left panel). Moreover, these effects did not appear in cells transfected with a DNA construct containing a mutation at the miR-448 binding site (FIG. 3, upper right and lower right panels). These results demonstrate that SCN5A is a direct target of miR-448.

SCN5A Expression was Regulated by miR-448

Next, the ability of miR-448 to regulate the expression and the function of Na$_v$1.5 (encoded by SCN5A) was investigated. In RL14 human cardiomyocytes, SCN5A mRNA expression was reduced by the miR-448 mimic and induced by anti-miR-448 (inhibitor) (FIG. 4A). Na$_v$1.5 protein level was also regulated by treatment of miR-448 mimic or an inhibitor in a manner consistent with miR-448 regulation of SCN5A mRNA (FIG. 4B).

Human iPSC-cardiomyocytes (CMs) were used to determine the effect of the miR-448 mimic on Na$_v$1.5-mediated sodium current. The SCN5A mRNA levels were reduced by transfection of the miR-448 mimic (FIG. 5A). The peak sodium current in miR-448-mimic-transfected iPSC-CMs was reduced compared with control infection (FIGS. 5B and 5C). Channel macroscopic activation or inactivation gating was not altered by either the control or the miR-448 mimic infections (FIG. 5D). Taken together, these results indicated that miR-448 could control the Na$_v$1.5 current level in addition to the SCN5A mRNA level.

Hypoxia-Induced miR-448 Controlled SCN5A

To investigate the regulation of SCN5A in hypoxic condition, RL14 cells were stimulated with deferoxamine (DFX). SCN5A mRNA expression was decreased by deferoxamine stimulation in a dose-dependent and time-dependent manner and Na$_v$1.5 protein level was also decreased by deferoxamine (FIG. 11).

A DNA construct with four miR-448 binding sites following the luciferase coding region (miR-448 decoy, illustrated in FIG. 6A) was used to inhibit the effect of miR-448 on SCN5A. EGFP DNA was used as a transfection control. Reduced luciferase mRNA level in deferoxamine-stimulated RL14 cells confirmed that the miR-448 decoy was effective in acting competitively against miR-448 increased by deferoxamine stimulation (FIG. 6A). The reduced mRNA expression of SCN5A was rescued by the miR-448 decoy treatment (FIG. 6B). The protein level of Na$_v$1.5 was also rescued in the cells transfected with the miR-448 decoy (FIG. 6C). These results indicated that SCN5A expression can be regulated by hypoxia-induced miR-448.

HIF1α and NF-κB Regulated miR-448 in Hypoxia

The MIR448 gene is located in an intron of the HTR2C gene, but MIR448 is regulated independently from HTR2C. Regulation of miR-448 expression by hypoxia investigated. A transcription factor binding site prediction tool (Lee et al., 2013, *Biotechniques* 54:141-153) suggested binding sequences for HIF1α and NF-κB within a 1 Kb from transcription initiation site of MIR448. HIF1α and NF-κB are well-known hypoxia response factors. Deferoxamine treatment of RL14 cardiomyocytes for six hours increased the protein level and the translocation into the nucleus of HIF1α and NF-κB (FIG. 12). KC7F2 (KC; HIF1α inhibitor) or Bay11-7028 (Bay; NF-κB inhibitor) inhibited the increased of miR-448 by deferoxamine (FIGS. 7A and 7B). To confirm this apparent transcriptional regulation, a series of three partial deletion mutants, −687 bp, −151 bp, or −92 bp promoter regions from the MIR448 transcriptional initiation site were constructed with the deletions upstream of the luciferase gene in the pGL3-Basic vector. Deletion of the promoter region from nucleotides −687 to −151 produced a dramatic reduction in transcriptional activity (FIG. 7C), indicating that this site, which contains HIF1α and NF-κB binding elements, mediates regulation of MIR448 expression. These results suggest that hypoxia-induced HIF1α and NF-κB can regulate MIR448 expression.

REST Suppressed miR-448

Within the 1 Kb MIR448 promoter was a predicted RE1 Silencing Transcription Factor (REST) binding site. REST was initially identified as a transcriptional repressor that regulates neuronal genes in non-neuronal tissues. REST regulates other genes in response to changes in oxygen tension by direct binding to an RE1/NRSE site on their promoter regions. In normoxia, MIR448 expression was increased by REST gene silencing (FIG. 8A), and SCN5A mRNA and Na$_v$1.5 protein level were decreased (FIG. 8B). Moreover, Na$_v$1.5 protein level was decreased by the REST specific inhibitor, X5050 (FIG. 8C). REST mRNA and protein were decreased by hypoxia (FIG. 8D). These results indicated that miR-448 expression is inhibited by REST in normoxia and that REST, together with HIF1α and NF-κB, regulates miR-448 in ischemia.

miR-448 Inhibition Raised Na$_v$1.5 and Reduced Arrhythmia in Myocardial Infarction Ischemia reduces Na$_v$1.5, and reduced Na$_v$1.5 is arrhythmogenic. Ischemia-induced miR-448 contributes to the reduction in Na$_v$1.5. Therefore, the effect of inhibiting miR-448 on Na$_v$1.5 levels and arrhythmic risk in ischemic cardiomyopathy was tested. Mice underwent LAD ligation to create myocardial ischemia and infarction. An miR-448 sponge was used to inhibit the function of miR-448. In human cardiomyocytes, sponge treatment rescued SCN5A mRNA levels decreased by miR-448 treatment, indicating the efficacy of this sponge approach (FIG. 13).

To test the role of miR-448 in regulating SCN5A expression in vivo, myocardial infarcted mice were injected with either AAV9-Control (Con) or AAV9-miR-448 sponge (448-Spo) viral particles two weeks before coronary artery ligation. To confirm gene expression in the heart through AAV9 injection, GFP expression was examined in the heart tissue of mice treated with an AAV9 vector encoding the GFP gene. The green fluorescence ratio increased compared to WT with AAV9-GFP treatment, and the GFP level also increased in the heart treated with AAV-GFP (FIG. 14). After two weeks of LAD ligation, the mouse hearts were harvested to evaluate the expression of SCN5A by RT-qPCR, Western blot, and immunohistochemistry. The cardiac mRNA level of SCN5A was increased in mice injected with 448-Spo as compared with in those injected with the Con (FIG. 9A). Also, the protein level of Na$_v$1.5 was increased in mice injected with 448-Spo (FIG. 9B). Spontaneous arrhythmias were observed in MI+Con mice. Arrhythmias were reduced with miR-448 inhibition by 448-Spo (FIG. 9D). These results indicated that miR-448 inhibition after myocardial infarction raises Na$_v$1.5 and reduces arrhythmic risk.

Mouse echocardiography was performed to confirm the myocardial infraction (MI) by LAD ligation. The ejection fraction (EF) of the MI+AAV9-Con group was reduced compared to the sham group, indicating that MI was present. AAV9-448-Spo treatment did not affect EF % change (FIG. 16). Infarct size was unchanged between mice with AAV9-Con and AAV9-448-Spo.

Arrhythmia is among the leading causes of death from ischemic cardiomyopathy. Arrhythmias are thought to be caused by structural and electrical remodeling. Electrical remodeling in the ventricle typically results from downregulation of ion channels by a variety of mechanisms including, for example, transcription, RNA processing, RNA stability, translation efficiency, and post-translational dysregulation. Reversing the ion channel downregulation can improve arrhythmic risk and may represent an alternative approach to ion channel blocking antiarrhythmic drugs.

Changes in SCN5A expression, either upregulation or downregulation, can cause arrhythmias, and SCN5A is downregulated in ischemic cardiomyopathy. Nevertheless, the mechanisms by which ischemia reduces SCN5A expression have not been fully explored but include mRNA destabilization. This disclosure describes investigating SCN5A mRNA instability during cardiac hypoxia and showed that the level of miR-448 increased during ischemia, miR-448 bound to SCN5A mRNA, and this binding reduced SCN5A mRNA, protein, and current. Moreover, this disclosure shows HIF1α and NF-κB upregulation and REST downregulation controlled miR-448 levels in response to hypoxia. Downregulation of SCN5A in ischemic cardiomyopathy was associated with increased arrhythmic risk, and miR-448 inhibition could restore $Na_v1.5$ levels and reduce arrhythmic risk.

Other miRs are known to regulate SCN5A. For example, SCN5A can be controlled by miRs targeting the gene coding region and the 3'-UTR. Also, miR-24 and miR-1270 can regulate expression by directly binding to binding sites created by single nucleotide polymorphisms (SNPs) of SCN5A. Also, miR-192-5p increases in atrial fibrillation (AF) and inhibits expression of SCN5A. Furthermore, miR-200c directly or indirectly regulates various cardiac genes including SCN5A. This disclosure shows that miR-448 directly bound to the SCN5A 3'-UTR and regulated the $Na_v1.5$ current.

This disclosure shows that miR-448 increases in hypoxic conditions and the miR-448 promoter region includes binding sites for hypoxia-related factors. The response to hypoxic stress is coupled tightly to the interaction between HIF1α and NF-κB signaling. Maximal HIF1α expression depends on transcriptional regulation by NF-κB and post-translational regulation by hypoxia. This disclosure shows that HIF1α and NF-κB binding sites were −530~−450 upstream from the miR-448 gene transcription initiation site and were involved in regulating miR-448 expression during hypoxia.

RE1 Silencing Transcription Factor (REST) can regulate genes in response to changes in oxygen tension. Reducing expression of REST contributes to gene upregulation in hypoxia. The MIR448 promoter analysis presented in this disclosure shows that the binding sequence for REST is within the 1 Kb region of the MIR448 promoter and that REST gene silencing in normoxia leads to an increase in miR-448 expression and a decrease in SCN5A expression. Therefore, there appears to be an interplay of relief of REST inhibition and increased of HIF1α and NF-κB induction to regulate miR-448 and, therefore, SCN5A. Consensus binding sequence analysis shows that REST may also be a target of miR-448, suggesting a more complex negative feedback loop.

In summary, miR-448 negatively regulated the cardiac sodium channel by direct binding to 3'-UTR of SCN5A mRNA. The effect of miR-448 increased in ischemia. Inhibition of miR-448 raised $Na_v1.5$ and reduced arrhythmic risk after myocardial infarction, suggesting a new paradigm in antiarrhythmic therapy.

Thus, this disclosure describes, in one aspect, a method of increasing translation of SCN5A mRNA in a cell. Generally, the method includes introducing into the cell an miR-448 inhibitor in an amount effective to decrease miR-448 suppression of SCN5A mRNA transcription. In some of these embodiments, the cell can be a cardiac cell. In such cases, increasing translation of SCN5A increases $Na_v1.5$ in the cell and reduces the extent and/or likelihood of arrythmia in the cardiac cell.

In another aspect, this disclosure describes a method of treating arrythmia in a patient having, or at risk of having, arrythmia. Generally, the method includes administering to the patient an miR-448 inhibitor in an amount effective to decrease the likelihood and/or extent of arrythmia in the patient.

Treating arrythmia by administering an miR-448 inhibitor can be prophylactic or, alternatively, can be initiated after the subject exhibits one or more symptoms or clinical signs of arrythmia. Treatment that is prophylactic—e.g., initiated before a subject manifests a symptom or clinical sign of arrythmia is referred to herein as treatment of a subject that is "at risk" of having arrythmia. As used herein, the term "at risk" refers to a subject that may or may not actually experience arrythmia. Thus, for example, a subject "at risk" of having arrythmia is a subject possessing one or more risk factors associated with arrythmia such as, for example, genetic predisposition, ancestry, age, sex, geographical location, lifestyle, or medical history. in some cases, a patient "at risk" for having arrythmia can be a patient who has a medical history that includes myocardial infarction.

Accordingly, a composition that includes an miR-448 inhibitor can be administered before, during, or after the subject first exhibits a symptom or clinical sign of arrythmia. Treatment initiated before the subject first exhibits a symptom or clinical sign of arrythmia may result in decreasing the likelihood that the subject experiences clinical evidence of arrythmia compared to a subject to which the composition is not administered, decreasing the severity of symptoms and/or clinical signs of arrythmia, and/or completely resolving the condition. Treatment initiated after the subject first exhibits a symptom or clinical sign associated with arrythmia may result in decreasing the severity of symptoms and/or clinical signs of arrythmia compared to a subject to which the composition is not administered, and/or completely resolving the condition.

Thus, the method includes administering an effective amount of an miR-448 inhibitor to a subject having, or at risk of having, arrythmia. In this aspect, an "effective amount" is an amount effective to reduce, limit progression, ameliorate, or resolve, to any extent, a symptom or clinical sign of arrythmia.

The miR-448 inhibitor may be formulated with a pharmaceutically acceptable carrier to form a pharmaceutical composition. As used herein, "carrier" includes any plasmid or viral vector, nanoparticle, microsome, lipid vector, chemical modification, solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with an miR-448 inhibitor without causing any undesirable biological effects or interacting in a deleterious manner with any of the other components of the pharmaceutical composition in which it is contained.

The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, organ injection, local injection, etc.), or topical (e.g., intranasal, intrapulmonary, intramammary, intravaginal, intrauterine, intradermal, transcutaneous, rectally, etc.). A pharmaceutical composition can be administered to a mucosal surface, such as by administration to, for example, the nasal or respiratory mucosa (e.g., by spray or aerosol). A composition also can be administered via a sustained or delayed release.

Thus, the miR-448 inhibitor may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a flavoring, a moisturizer, a thickener, and the like.

A formulation may be conveniently presented in unit dosage form and may be prepared by methods well known in the art of pharmacy. Methods of preparing a composition with a pharmaceutically acceptable carrier include the step of bringing the miR-448 inhibitor into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

The amount of miR-448 inhibitor administered can vary depending on various factors including, but not limited to, the specific miR-448 inhibitor, the weight, physical condition, and/or age of the subject, and/or the route of administration. Thus, the absolute amount of miR-448 inhibitor included in a given unit dosage form can vary widely, and depends upon factors such as the species, age, weight and physical condition of the subject, and/or the method of administration. Accordingly, it is not practical to set forth generally the amount that constitutes an amount of miR-448 inhibitor effective for all possible applications. Those of ordinary skill in the art, however, can readily determine the appropriate amount with due consideration of such factors.

In some embodiments, the method can include administering sufficient miR-448 inhibitor to provide a dose of, for example, from about 100 ng/kg to about 80 mg/kg. If delivered to the subject using a vector, the miRNA inhibitor may be administered in an amount up to $5 \times 10^{11}$ plaque forming units per kg or up to $1 \times 10^{15}$ vector genome (vg)/kg. In some of these embodiments, the method includes administering sufficient miR-448 inhibitor to provide a dose of from about 10 µg/kg to about 80 mg/kg to the subject, for example, a dose of from about 100 µg/kg to about 1 mg/kg. In other embodiments, the method includes administering sufficient miR-448 inhibitor to provide a dose of from about $1 \times 10^{11}$ to about $1 \times 10^{13}$ vg/kg.

A single dose may be administered all at once, continuously for a prescribed period of time, or in multiple discrete administrations. When multiple administrations are used, the amount of each administration may be the same or different. For example, a dose of 1 mg/kg per day may be administered as a single administration of 1 mg/kg, continuously over 24 hours, as two 0.5 mg/kg administrations, or as a first administration of 0.75 mg/kg followed by a second administration of 0.25 mg/kg. When multiple administrations are used to deliver a single dose, the interval between administrations may be the same or different.

In some embodiments, the miR-448 inhibitor may be administered, for example, from a single dose to multiple doses per week, although in some embodiments the method can involve a course of treatment that includes administering doses of the miR-448 inhibitor at a frequency outside this range. When a course of treatment involves administering multiple within a certain period, the amount of each dose may be the same or different. For example, a course of treatment can include a loading dose initial dose, followed by a maintenance dose that is lower than the loading dose. Also, when multiple doses are used within a certain period, the interval between doses may be the same or be different.

In certain embodiments, the miR-448 inhibitor may be administered from about once per month to continuously. For example, an miR-448 inhibitor may be administered once following acute myocardial infarction. In contrast, an miR-448 inhibitor may be administered chronically for treating cardiomyopathy.

In all aspects, the miR-448 inhibitor may be any polynucleotide, compound, or molecule that interferes with the ability of miR-448 to suppress translation of SCN5A mRNA. Exemplary miR-448 inhibitors include, but are not limited to, a commercially-available miR-448 inhibitor, an miR-448 antagomir, an miR-448 sponge, am miRN mask, or any combination of two or more miR-448 inhibitors.

miRNA inhibitors are also known as anti-miRNAs. miRNA inhibitors are single-stranded RNA molecules. As illustrated in FIG. 18, anti-miRNAs can specifically bind to endogenous miRNA and suppress the activity of the endogenous miRNA. Exemplary commercially-available miR-448 inhibitors include, but are not limited to, MISSION® synthetic miRNA inhibitor, Human-has-miR-448-5p (Millipore-Sigma, Billerica, MA), AMBION™ hsa-miR-448-5p (Thermo Fisher Scientific, Inc., Waltham, MA), mirVana™ hsa-miR-448-5p (Thermo Fisher Scientific, Inc., Waltham, MA), and miRCURY™ LNA miRNA inhibitor, hsa-miR-448 (Qiagen, Hilden, Germany), miARREST™ miRNA inhibitors as vector-based expression clones or synthetic oligonucleotides (GeneCopoeia, Inc., Rockville, MD), a custom miRNA inhibitor (Creative Biolabs, Inc., Shirley, NY), an miRNA mimic inhibitor (GenePharma Co., Ltd., Shanghai, China).

Antagomirs are single-stranded RNA molecules with specific chemical modifications. As illustrated in FIG. 20, modifications in an antagomir can include a 2-phosphorothioate are introduced at the 5' end, a cholesterol group introduced at the 5' end, and/or a 4-phosphorothioate introduced at the 3' end. Moreover, one or more 2'-methoxy groups can be introduced anywhere along the oligonucleotides. Any individual antagomir can include one or more of the foregoing chemical modifications. When more than one chemical modification is present, the antagomir can include any combination of chemical modifications. Each of these chemical modifications, individually or in any combination, enhance the stability and cellular uptake efficiency of antagomirs. Therefore, miRNA antagomirs can be used in vivo via either local or systemic administration to downregulate the corresponding endogenous miRNA levels. Exemplary anti-miR-448 antagomirs include, but are not limited to, MIRACLE hsa-miR-448 antagomir (AcceGen, Fairfield, NJ) and RNA oligonucleotides containing 2'-O-methyl residues (Integrated DNA Technologies, Inc., Coralville, IA).

An miRNA sponge, illustrated in FIG. 19, is a polynucleotide—typically a plasmid-encoded—that contains multiple binding sites complementary to the seed region of the target miRNA (FIG. 14). After being transfected into a cell, a plasmid encoding an miRNA sponge can transcribe high levels of sponge RNAs that bind to the seed region, which allows them to block a family of miRNAs containing the same seed sequence. As competitive inhibitors, miRNA sponges exhibit similar inhibition efficiency with short nucleotide fragments. miRNA sponges are available from, for example, Creative Biolabs, Inc. (Shirley, NY) and Acce-Gen, (Fairfield, NJ)

In the preceding description and following claims, the term "and/or" means one or all of the listed elements or a combination of any two or more of the listed elements; the terms "comprises," "comprising," and variations thereof are to be construed as open ended i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Cell Culture and Transfection

Human fetal cardiomyocyte cell line RL14 (ATCC RL-14, ATCC, Manassas, VA) cells were grown in DMEM/F-12 nutrient mixture (GE Healthcare Life Sciences, Logan, UT) supplemented with 12.5% (v/v) fetal bovine serum (Gibco, Grand Island, NY) and penicillin-streptomycin (10,000 U/mL; Gibco, Grand Island, NY). HEK293T cells were maintained in DMEM high glucose supplemented with 10% fetal bovine serum and penicillin-streptomycin. hiPSC-cardiomyocytes (iCELL Cardiomyocytes) were obtained from Cellular Dynamics International (Madison, WI). iCELL cardiomyocytes were seeded and maintained using iCELL Cardiomyocyte Plating Medium and Maintenance Medium (FUJIFILM Cellular Dynamics, Inc., Madison, WI). For hypoxic conditions, the cells were cultured in an hypoxic incubator chamber (STEMCELL Technologies, Vancouver, BC) using pre-incubated culture media or were treated with hypoxic-mimetic chemicals, deferoxamine (DFX) and cobalt chloride ($CoCl_2$) (Sigma-Aldrich, St. Louis, MO) as previously described (Chachami et al., 2004, *Am J Respir Cell Mol Biol* 31:544-551; Woo et al, 2006, *Biochem Biophys Res Commun* 343:8-14).

Cell Transfection

Syn-hsa-miR-448 miScript miRNA mimic, anti-hsa-miR-448 miScript miRNA inhibitor, and its negative controls were purchased from Qiagen (Valencia, CA). REST siRNA and its negative control were obtained from Integrated DNA Technologies (Coralville, IA). The cells were transfected using HiPerFect Transfection Reagent (Qiagen, Valencia, CA) following the recommendations of the manufacturer. Plasmid DNA was transfected into cultured cells using SuperFect transfection reagent (Qiagen, Valencia, CA) following the manufacturer's protocol.

Plasmid Constructions

Gene fragments for SCN5A 3'-UTR with or without mutations at the miR-448 binding site were obtained from Integrated DNA Technologies (IDT, Coralville, IA). They were cloned into pGL3-Promoter vectors downstream of the luciferase open reading frame to create pGL3-Promoter-Luciferase SCN5A 3'-UTR wild type (WT) or mutation (Mut) vectors. A gene fragment for miR-448 acted as a decoy, was obtained from IDT, and was cloned into pcDNA3.1 (+) luciferase vector downstream of the luciferase open reading frame to create a pcDNA3.1(+)-Luciferase-miR-448 decoy vector. The miR-448 decoy sequence was designed and confirmed using the "miRNAsong" web tool (Barta et al., 2016, *Sci Rep* 6:36625). A gene fragment for a 1 Kb promoter region of miR-448 was obtained from Integrated DNA Technologies (Coralville, IA) and cloned into the pGL3-Basic vector upstream of the luciferase open reading frame to create a pGL3-MIR448 promoter-Luciferase vector. Then, −687 bp, −151 bp, and −92 bp DNA fragments were amplified by PCR with specific primers and were cloned into the pGL3-Basic vector. All DNA constructs were confirmed by DNA sequencing.

Each DNA construct was transfected into cardiomyocytes, and the cells were stimulated with deferoxamine for six hours. Luciferase mRNA level was detected by qPCR. The mRNA level of luciferase was normalized with the mRNA level of EGFP which was co-transfected as a control.

RNA Preparation and Real-Time Reverse Transcription Polymerase Chain Reaction

Total RNA was prepared using RNeasy Plus Mini Kit or miRNeasy Mini Kit (Qiagen, Valencia, CA) according to the manufacturer's instructions. Reverse transcription was performed with a First Strand cDNA Synthesis kit (Promega, Madison, WI). cDNA for miRNA detection was generated by the miScript II RT Kit (Qiagen, Valencia, CA). A reverse transcription quantitative real-time PCR was performed with SYBR Green PCR Master Mix (Thermo Fisher Scientific, Waltham, MA) using the 7500Fast Real-Time PCR system (Thermo Fisher Scientific, Waltham, MA) and miScript SYBR Green PCR Kit with miScript primer assays to detect the expression of miRNA. The primer sequences were as follows:

```
SCN5A
F
                              (SEQ ID NO: 4)
5'-TGGTTGTCATCCTCTCCATCGT-3'

R
                              (SEQ ID NO: 5)
5'-ATGAGGGCAAAGAGCAGCGT-3'

GAPDH
F
                              (SEQ ID NO: 6)
5'-GAAGGTGAAGGTCGGAGTCAAC-3'
```

15

-continued

R (SEQ ID NO: 7)

5'-CAGAGTTAAAAGCAGCCCTGGT-3'

Hs_miR-448_1 miScript Primer Assay (5'-UUGCAUAU-GUAGGAUGUCCCAU-3'; (SEQ ID NO:1; Qiagen, Valencia, CA) was used for detecting miR-448, and the Hs_RNU6-2_11 miScript Primer Assay (Qiagen, Valencia, CA) was used as an endogenous control. The relative fold change was calculated by the $2^{-\Delta\Delta Ct}$ method, and the measurements were normalized with respect to the endogenous control (RNU6, GAPDH).

Western Blot

Cells were washed twice with ice-cold PBS and disrupted in Cell Lysis Buffer (Cell Signaling Technology, Danvers, MA) with Protease and Phosphatase Inhibitor Cocktail (Thermo Fisher Scientific, Waltham, MA) on ice for 30 minutes. Cell lysates were centrifuged at 14,000 rpm for 15 minutes at 4° C., and the resultant supernatants were subjected to Western blotting. The total protein concentration was quantified using the BCA Protein Assay Kit (Pierce, Thermo Fisher Scientific, Waltham, MA). Proteins were separated by electrophoresis on a 4-15% Mini-PROTEAN TGX Precast Protein Gels (Bio-Rad Laboratories, Inc., Hercules, CA), after which samples were transferred onto a polyvinylidene difluoride (PVDF) membrane. The membrane was treated with 5% skim milk for one hour and incubated with Na$_v$1.5 antibody (1:1000 dilution; ab56240, Abcam, Cambridge, MA), HIF1$\alpha$ (1:1000 dilution; ab72775, Abcam, Cambridge, MA), NF-$\kappa$B (1:1000 dilution; ab32536, Abcam, Cambridge, MA), REST (1:1000 dilution; ab21635, Abcam, Cambridge, MA), or $\beta$-actin (1:5000 dilution; A5441, Sigma-Aldrich, St. Louis, MO) overnight at 4° C.

After TBST washing, the membrane was incubated with horseradish peroxidase (HRP)-conjugated secondary antibody (1:5000) for 90 min at room temperature. The proteins were visualized with Pierce ECL Western Blotting Substrate (Thermo Fisher Scientific, Waltham, MA) using the CHEMIDOC XRS+ System (Bio-Rad Laboratories, Inc., Hercules, CA). The images were analyzed using ImageJ software to measure band density. Band density was normalized with 3-actin from three independent experiments.

Electrophysiology hiPSC-cardiomyocytes (CMs) were trypsinized (0.25% trypsin-EDTA, Invitrogen) for 10 minutes and plated in 35-mm culture dishes at a cell density of ~100 cells/dish on the day before the experiments. Na$^+$ channel currents were measured by using the whole-cell patch-clamp technique in the voltage-clamp configuration at room temperature. hiPSC-CMs were not selected by action potential morphology, but the differentiation technique resulted in predominantly ventricular-like cells. To measure Na$^+$ channel currents, pipettes (2 to 4 M$\Omega$) were filled with a pipette solution containing (in mmol/L): CsCl 80, cesium aspartate 80, EGTA 11, MgCl2 1, CaCl2) 1, HEPES 10, and Na2ATP 5 (adjusted to pH 7.4 with CsOH). The bath solution consisted of (in mmol/L): NaCl 10, NMDG 100, TEA-Cl 20, CsCl 5, CaCl$_2$) 2, MgCl2 1.2, HEPES 10, and glucose 5 (adjusted to pH 7.4 with CsOH). The holding potential was –100 mV. A voltage step protocol ranging from –80 to +60 mV with steps of 10 mV was applied to establish the presence of the Na$^+$ channel currents. The peak current density was used to plot current-voltage (I-V) curves. As before, nifedipine (10 $\mu$M, Sigma) was added in the bath solution to block L-type Ca$^{2+}$ channel currents. Steady state activation and inactivation were characterized by Boltzmann functions.

Human Samples

Deidentified control heart tissue was a gift of Prof. J. A. Wasserstrom of Northwestern University. All control heart tissue was derived from patients suffered brain death because of a cerebral vascular accident and had no concomitant cardiac conditions before the heart was harvested.

Deidentified HF heart tissues were obtained from Lillehei Heart Institute tissue bank at the University of Minnesota. HF patients had a history of ischemic cardiomyopathy that was confirmed by histological specimens prepared concomitantly with acquisition of the specimen. In the control and HF groups, specimens were from the left ventricle. Arrhythmic status was determined by record review.

Mouse Cardiac Ischemia Model

In order to create ischemia, mice underwent left anterior coronary artery (LAD) ligation as previously described (Zhou et al., 2018, Heart Rhythm 15:1072-1080). Eight-week-old male C57BL/6 mice were randomly divided into the MI group and MI+miR-448 sponge AAV9 group. To investigate whether miR-448 inhibition is sufficient to prevent arrhythmia in vivo, adeno-associated virus serotype 9 (AAV9) viral particles bearing either an empty vector or anti-miR-448 were systemically injected into mice via the right jugular vein (VectorBuilder Inc, IL) at a dose of 5×10$^{11}$ viral genomes (vg) per animal before LAD ligation. All animal protocols used in this study were approved by the IACUC (Institutional Animal Care and Use Committee) of University of Minnesota. Animal care and interventions were undertaken in accordance with the National Institute of Health (NIH) Guide for the Care and Use of Experimental Animals.

Telemetry Monitoring

Three randomly selected MI+control or MI+anti-miR-448 mice were implanted with ETA-F10 transmitters (Data Sciences International, St. Paul, MN). Mice were anesthetized with 4% and maintained on 2% inhaled isoflurane. A skin incision was made in the right abdominal region, and a transmitter was inserted subcutaneously. The two electrocardiographic leads were tunneled and positioned under the skin to generate a lead II electrocardiographic configuration. One week after transmitter implantation, electrocardiographic signals were recorded for 24 hours. Heart rate calculations and cardiac rhythm analysis were performed by using Dataquest ART, version 4.1 (Data Sciences International, St. Paul, MN) and LabChart 7 Pro, version 7.3.7 (AD Instruments, Inc., Colorado Springs, CO) (Kannankeril et al., 2006, Proc Natl Acad Sci USA, 103:12179-12184; Xie et al., 2018, J Am Heart Assoc 7(8)).

For arrhythmia provocations, isoproterenol (ISO) was injected into the peritoneum (IP; 0.2 mg/kg). After establishing the baseline rhythm for 24 hours, each mouse received ISO and the ECG was recorded for another two hours. ECGs were analyzed beginning 60 minutes before intraperitoneal injection of isoproterenol as a baseline, and then for 60 minutes after injection to identify isoproterenol-induced arrhythmias.

ECG signal analysis was performed blinded to treatment.

Immunohistochemistry

The heart tissues were fixed in 4% paraformaldehyde (pH7.4) for 24 hours, embedded in paraffin, and serially sectioned to 5 m thickness. For the dewaxing process, the paraffin sections were placed at 60° C. overnight and then transferred to xylene (10 minutes, three times), anhydrous ethanol (three minutes, twice), 95% ethanol (one minute, once), 70% ethanol (one minute, once), and distilled water (two minutes, once). The tissue sections were heated with citrate buffer (pH 6.0) for five minutes at 100° C. After rinsing using washing buffer, the sections were incubated in 3% hydrogen peroxide to quench endogenous peroxidase activity and blocked with 3% bovine serum albumin (BSA, Bio-Rad Laboratories, Inc., Hercules, CA) to prevent non-specific antibody binding. Next, the tissue sections were incubated with primary antibodies against GFP (1:200 dilution; sc-9996, Santa Cruz Biotechnology, Dallas, TX) and Na$_v$1.5 (1:200 dilution, ab56240, Abcam) at 4° C. overnight and HRP-conjugated secondary antibodies (Bio-Rad Laboratories, Inc., Hercules, CA) for 30 minutes at room temperature. Finally, the sections were incubated with 3, 3'-diaminobenzidine (DAB) peroxidase substrate kit (Vector Laboratories, Inc., Burlingame, CA) and counterstained with hematoxylin (Vector Laboratories, Inc., Burlingame, CA). After permanent mounting, the sections were imaged using a light microscope (Axioscope 7, Zeiss; Jena, Germany). In captured image, the regions of interest (ROI) were demarcated using ZEN Pro software (Zeiss). Quantitative analysis was performed using Image Pro Plus software (version 6.0; Media Cybernetics, Bethesda, MD).

Statistics

Statistical significance between groups was performed using Student's t-tests (paired and unpaired), one-way analysis of variance (ANOVA) with Dunnett's multiple comparisons test where appropriate. For all analyses, a p-value of less than 0.05 was considered significant. All data were analyzed using Prism software (version 8.0, GraphPad Software, San Diego, CA) and R. The data presented represent the mean+ or ±standard deviation (SD). A p value <0.05 was considered statistically significant.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

```
SEQ ID NO: 1 - hsa-miR-448
uugcauaugu aggauguccc au

SEQ ID NO: 2 - SCN5A 3'-UTR (wt)
gacaauccua uuuagcauau gcaa

SEQ ID NO: 3 - SCN5A 3'-UTR (mutant)
gacaauccua uuuagcuaua cqua

SEQ ID NO: 4 - SCN5A forward primer
TGGTTGTCATCCTCTCCATCGT

SEQ ID NO: 5 - SCN5A reverse primer
ATGAGGGCAAAGAGCAGCGT

SEQ ID NO: 6 - GADPH forward primer
GAAGGTGAAGGTCGGAGTCAAC

SEQ ID NO: 7 - GADPH reverse primer
CAGAGTTAAAAGCAGCCCTGGT
```

What is claimed is:

1. A method of treating arrhythmia in a human patient having, or at risk of having, arrhythmia, the method comprising:

administering to the human patient an miR-448 antagomir or an miR-448 sponge in an amount effective to decrease the likelihood or extent of arrhythmia in the patient, wherein the patient has experienced myocardial infarction.

* * * * *